(12) United States Patent
Tanaka et al.

(10) Patent No.: US 9,592,023 B2
(45) Date of Patent: Mar. 14, 2017

(54) X-RAY CT APPARATUS AND TOMOGRAPHY METHOD

(71) Applicant: HITACHI, LTD., Tokyo (JP)

(72) Inventors: Kana Tanaka, Tokyo (JP); Koichi Hirokawa, Tokyo (JP); Yukio Kumagai, Tokyo (JP); Ryo Yoshida, Tokyo (JP)

(73) Assignee: HITACHI, LTD, Tokyo (JP)

( * ) Notice: Subject to any disclaimer, the term of this patent is extended or adjusted under 35 U.S.C. 154(b) by 55 days.

(21) Appl. No.: 14/440,766

(22) PCT Filed: Nov. 28, 2013

(86) PCT No.: PCT/JP2013/081989
§ 371 (c)(1),
(2) Date: May 5, 2015

(87) PCT Pub. No.: WO2014/084291
PCT Pub. Date: Jun. 5, 2014

(65) Prior Publication Data
US 2015/0297165 A1 Oct. 22, 2015

(30) Foreign Application Priority Data
Nov. 30, 2012 (JP) ................................. 2012-262580

(51) Int. Cl.
*A61B 6/03* (2006.01)
*A61B 6/00* (2006.01)
(Continued)

(52) U.S. Cl.
CPC ............ *A61B 6/5258* (2013.01); *A61B 6/032* (2013.01); *A61B 6/035* (2013.01); *A61B 6/405* (2013.01);
(Continued)

(58) Field of Classification Search
CPC ......... A61B 6/032; A61B 6/405; A61B 6/542; A61B 6/544; A61B 6/545; A61B 6/4035; A61B 6/4085; A61B 6/465; A61B 6/467
See application file for complete search history.

(56) References Cited

U.S. PATENT DOCUMENTS 8,768,030 B2* 7/2014 Bruder .................. A61B 6/032
378/10
8,861,674 B2* 10/2014 Koehler ................ A61B 6/032
378/4

(Continued)

FOREIGN PATENT DOCUMENTS

JP 2010-142477 7/2010
JP 2010-193940 9/2010
(Continued)

*Primary Examiner* — David A Vanore
(74) *Attorney, Agent, or Firm* — Cooper & Dunham LLP

(57) ABSTRACT

In an X-ray CT apparatus, a tube current value calculation unit calculates a tube current value of an X-ray tube based on a successive approximation process condition and based on an input scanning condition and/or a reconstruction condition. A scanning control unit performs scanning based on the calculated tube current value of the X-ray tub, and an image reconstruction unit reconstructs a tomographic image of an object, in accordance with the selected successive approximation process condition and the reconstruction condition. The tomographic image is reconstructed from an amount of transmitted X-rays detected by an X-ray detector after being emitted from an X-ray source to the object, in accordance with the calculated tube current value of the X-ray tube, and being transmitted through the object.

18 Claims, 30 Drawing Sheets

(51) Int. Cl.
*G06T 7/00* (2006.01)
*H05G 1/34* (2006.01)
*H05G 1/46* (2006.01)

(52) U.S. Cl.
CPC ............ *A61B 6/488* (2013.01); *A61B 6/5205* (2013.01); *A61B 6/5294* (2013.01); *A61B 6/54* (2013.01); *A61B 6/542* (2013.01); *A61B 6/544* (2013.01); *A61B 6/545* (2013.01); *G06T 7/0012* (2013.01); *H05G 1/34* (2013.01); *H05G 1/46* (2013.01); *A61B 6/4435* (2013.01); *G06T 2207/10081* (2013.01); *G06T 2207/10144* (2013.01); *G06T 2207/30004* (2013.01)

(56) References Cited

U.S. PATENT DOCUMENTS

| | | | | |
|---|---|---|---|---|
| 8,891,849 | B2* | 11/2014 | Rohler | A61B 6/032 382/132 |
| 8,965,092 | B2* | 2/2015 | Hoernig | G06K 9/78 378/16 |
| 8,971,607 | B2* | 3/2015 | Goto | G06T 11/003 382/131 |
| 8,989,469 | B2* | 3/2015 | Fahimian | A61B 6/032 378/19 |
| 9,008,274 | B2* | 4/2015 | Stevens | A61B 6/52 378/4 |
| 9,036,771 | B2* | 5/2015 | Yu | A61B 6/5258 378/19 |
| 9,042,512 | B2* | 5/2015 | Yin | A61B 6/032 250/370.09 |
| 9,042,626 | B1* | 5/2015 | Katsevich | A61B 6/503 382/131 |
| 9,050,003 | B2* | 6/2015 | Takahashi | A61B 6/032 |
| 9,113,799 | B2* | 8/2015 | Katsumata | A61B 6/032 |
| 9,123,098 | B2* | 9/2015 | Takahashi | A61B 6/032 |
| 9,123,156 | B2* | 9/2015 | Takahashi | G06T 11/006 |
| 9,125,572 | B2* | 9/2015 | Noo | A61B 6/027 |
| 9,155,508 | B2* | 10/2015 | Ueki | A61B 6/032 |
| 9,173,617 | B2* | 11/2015 | Hough | A61B 6/032 |
| 9,198,626 | B2* | 12/2015 | Heuscher | A61B 6/032 |
| 9,254,107 | B2* | 2/2016 | Sugaya | A61B 6/032 |
| 9,259,191 | B1* | 2/2016 | Noo | G21K 1/02 |
| 9,295,437 | B2* | 3/2016 | Saito | G21K 1/046 |
| 9,332,946 | B2* | 5/2016 | Heuscher | A61B 6/032 |
| 9,364,191 | B2* | 6/2016 | Ning | A61B 6/4241 |
| 9,380,987 | B2* | 7/2016 | Kojima | G01T 1/2002 |
| 9,420,986 | B2* | 8/2016 | Yamakawa | A61B 6/5235 |
| 2013/0028500 | A1 | 1/2013 | Takahashi et al. | |
| 2013/0156151 | A1 | 6/2013 | Sugaya et al. | |

FOREIGN PATENT DOCUMENTS

| | | |
|---|---|---|
| WO | WO2011/122613 | 10/2011 |
| WO | WO2012/033028 | 3/2012 |

\* cited by examiner

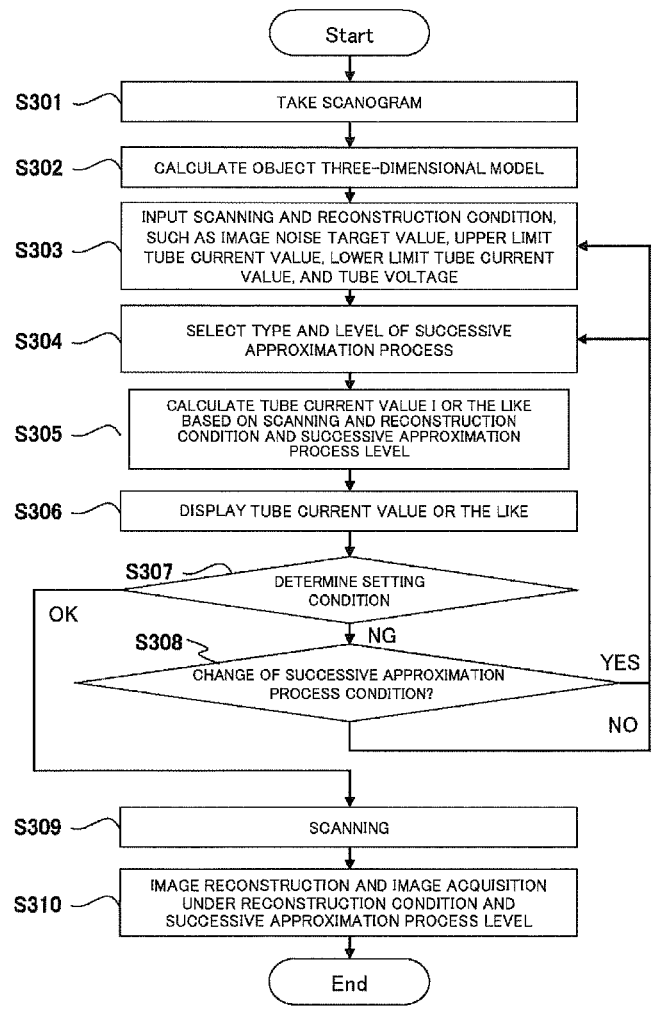

| ITEM | VALUE |
|---|---|
| SUCCESSIVE APPROXIMATION PROCESS LEVEL | 5 |
| IMAGE NOISE TARGET VALUE [HU] | 10.0 |
| UPPER LIMIT TUBE CURRENT VALUE | 500 |
| LOWER LIMIT TUBE CURRENT VALUE | 100 |
| PREDICTED AVERAGE IMAGE NOISE VALUE [HU] | |
| REQUIRED MAXIMUM TUBE CURRENT VALUE [mA] | |
| REQUIRED MINIMUM TUBE CURRENT VALUE [mA] | |
| AVERAGE TUBE CURRENT VALUE [mA] | |
| TUBE CURRENT VALUE REDUCTION RATE | |
| CTDI [mGy] | |
| IMAGE RECONSTRUCTION TIME [s] | |
| BREATH-HOLD TIME [s] | |

HU : Hounsfield Unit   301 [CONFIRM]   [TYPE CHANGE] 303

300, 310, 320

(B)

| ITEM | VALUE |
|---|---|
| SUCCESSIVE APPROXIMATION PROCESS LEVEL | 5 |
| IMAGE NOISE TARGET VALUE [HU] | 10.0 |
| UPPER LIMIT TUBE CURRENT VALUE | 500 |
| LOWER LIMIT TUBE CURRENT VALUE | 100 |
| PREDICTED AVERAGE IMAGE NOISE VALUE [HU] | 10.0 |
| REQUIRED MAXIMUM TUBE CURRENT VALUE [mA] | 480 |
| REQUIRED MINIMUM TUBE CURRENT VALUE [mA] | 250 |
| AVERAGE TUBE CURRENT VALUE [mA] | 400 |
| TUBE CURRENT VALUE REDUCTION RATE | 50% |
| CTDI [mGy] | 11.6 |
| IMAGE RECONSTRUCTION TIME [s] | 20 |
| BREATH-HOLD TIME [s] | 10 |

HU : Hounsfield Unit   301 [CONFIRM]   [TYPE CHANGE] 303

FIG.5

| TYPE | TUBE CURRENT VALUE CALCULATION METHOD |
|---|---|
| TYPE 1 | WHEN TUBE CURRENT VALUE REDUCTION RATE DEPENDS ON TUBE VOLTAGE AND SUCCESSIVE APPROXIMATION PROCESS LEVEL |
| TYPE 2 | WHEN TUBE CURRENT VALUE REDUCTION RATE DEPENDS ON FIELD-OF-VIEW SIZE AND SUCCESSIVE APPROXIMATION PROCESS LEVEL |
| TYPE 3 | WHEN TUBE CURRENT VALUE REDUCTION RATE DEPENDS ON IMAGE NOISE AND SUCCESSIVE APPROXIMATION PROCESS LEVEL |

301 — CONFIRM

FIG.18

\* SETTING PARAMETERS OF OPERATOR

500

|  | (1) SETTING CONDITION | (2) RECOMMENDED CONDITION | (3) RECOMMENDED CONDITION |
|---|---|---|---|
| \* SUCCESSIVE APPROXIMATION PROCESS LEVEL | 3 | 5 | 3<br>DURING POST-RECONSTRUCTION:5 |
| \* IMAGE NOISE TARGET VALUE [HU] | 10.0 | 10.0 | 11.8 |
| PREDICTED AVERAGE IMAGE NOISE VALUE [HU] | 10.7 | 10.0 | 11.8<br>DURING POST-RECONSTRUCTION :10.0 |
| \* UPPER LIMIT TUBE CURRENT VALUE [mA] | 500 | 500 | 500 |
| \* LOWER LIMIT TUBE CURRENT VALUE [mA] | 100 | 100 | 100 |
| REQUIRED MAXIMUM TUBE CURRENT VALUE [mA] | 670 | 480 | 480 |
| REQUIRED MINIMUM TUBE CURRENT VALUE [mA] | 350 | 250 | 250 |
| AVERAGE TUBE CURRENT VALUE [mA] | 470 | 400 | 400 |
| IMAGE RECONSTRUCTION TIME [s] | 30 | 50 | 30 |

HU : Hounsfield Unit

FIG.19
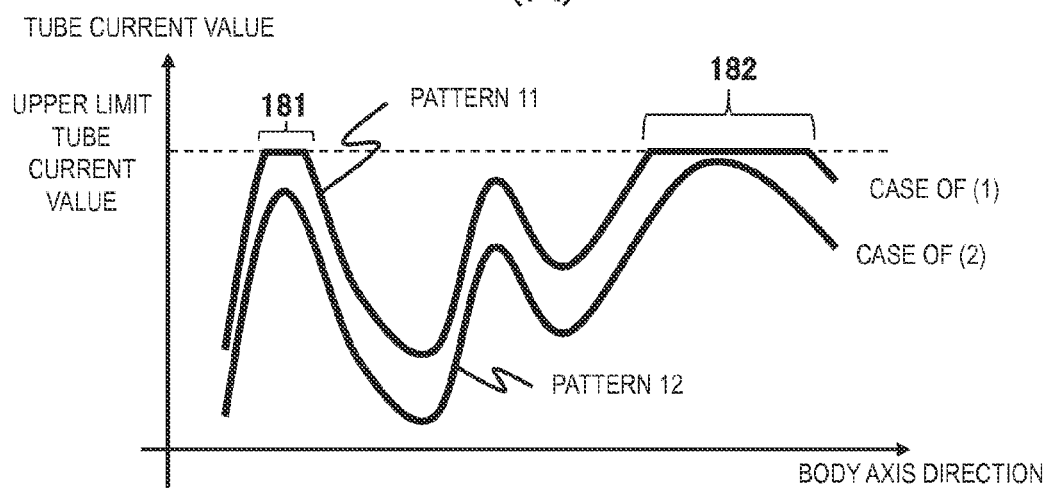
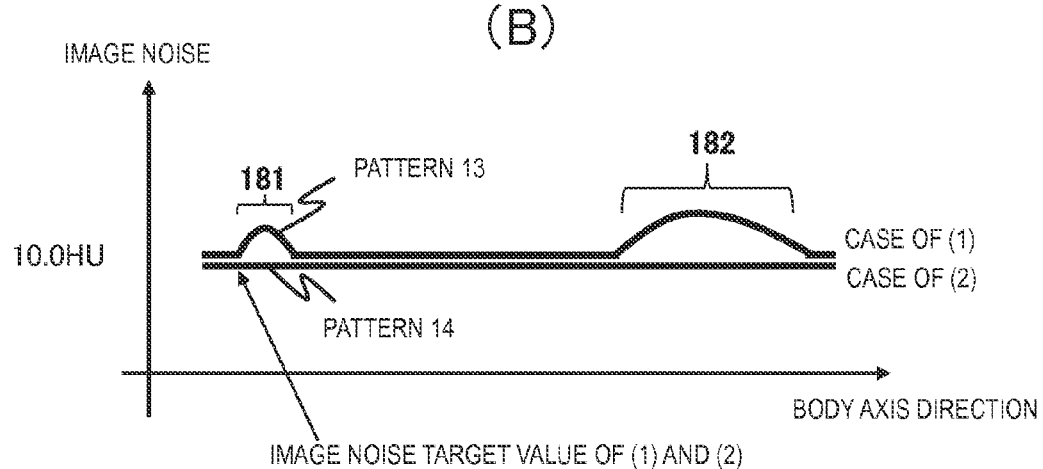

FIG.20
(A)
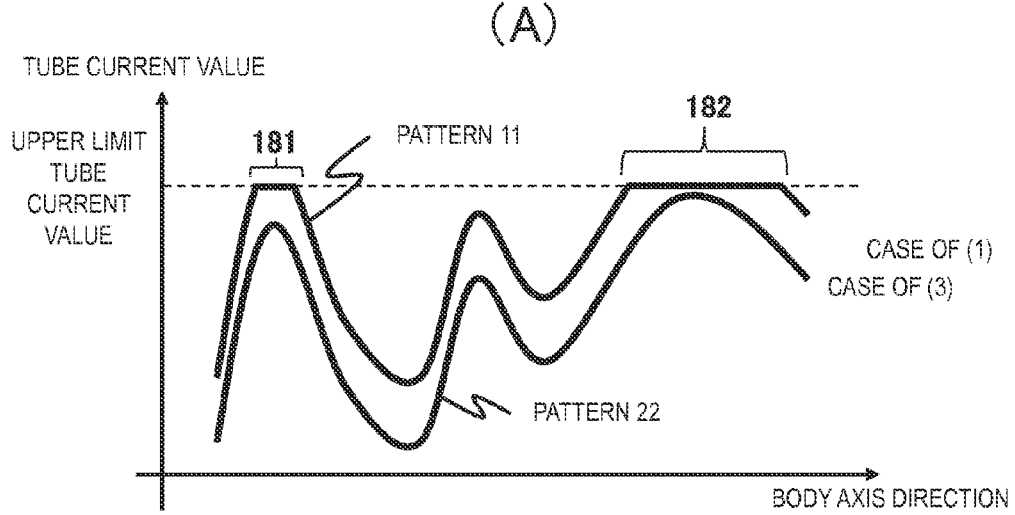
(B)
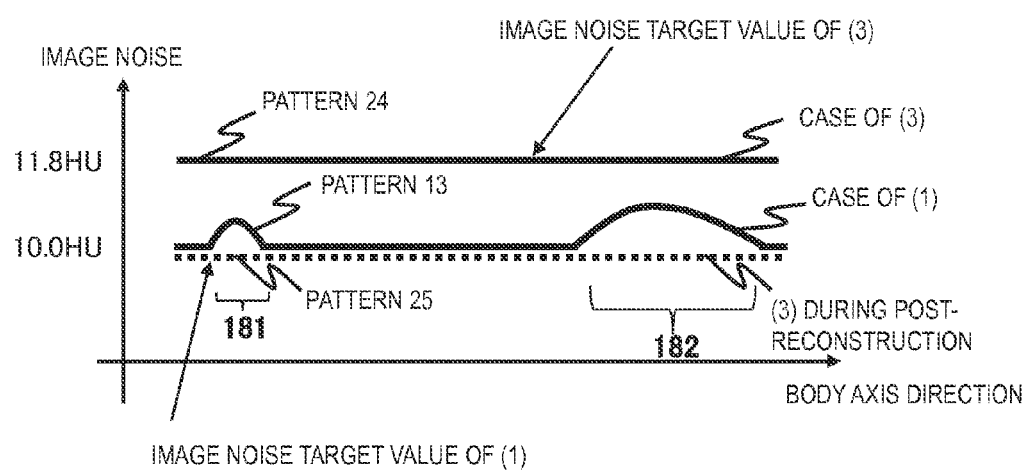

600

| PART | TUBE VOLTAGE | WEIGHT | RECOMMENDED LEVEL |
|---|---|---|---|
| LUNG FIELD | ALL kV | LESS THAN 40 kg | 7 |
| LUNG FIELD | ALL kV | 40 kg OR MORE AND LESS THAN 80 kg | 6 |
| LUNG FIELD | ALL kV | 80 kg OR MORE | 5 |
| ABDOMEN | LESS THAN 120 kV | LESS THAN 40 kg | 6 |
| ABDOMEN | LESS THAN 120 kV | 40 kg OR MORE AND LESS THAN 80 kg | 5 |
| ABDOMEN | LESS THAN 120 kV | 80 kg OR MORE | 4 |
| ABDOMEN | 120 kV OR MORE | LESS THAN 40 kg | 5 |
| ABDOMEN | 120 kV OR MORE | 40 kg OR MORE AND LESS THAN 80 kg | 4 |
| ABDOMEN | 120 kV OR MORE | 80 kg OR MORE | 3 |

| PART | TUBE VOLTAGE | WEIGHT | RECOMMENDED LEVEL |
|---|---|---|---|
| LUNG FIELD | ALL kV | LESS THAN 40 kg | 5 |
| LUNG FIELD | ALL kV | 40 kg OR MORE AND LESS THAN 80 kg | 4 |
| LUNG FIELD | ALL kV | 80 kg OR MORE | 3 |
| ABDOMEN | LESS THAN 120 kV | LESS THAN 40 kg | 5 |
| ABDOMEN | LESS THAN 120 kV | 40 kg OR MORE AND LESS THAN 80 kg | 4 |
| ABDOMEN | LESS THAN 120 kV | 80 kg OR MORE | 3 |
| ABDOMEN | 120 kV OR MORE | LESS THAN 40 kg | 4 |
| ABDOMEN | 120 kV OR MORE | 40 kg OR MORE AND LESS THAN 80 kg | 3 |
| ABDOMEN | 120 kV OR MORE | 80 kg OR MORE | 2 |

FIG.26
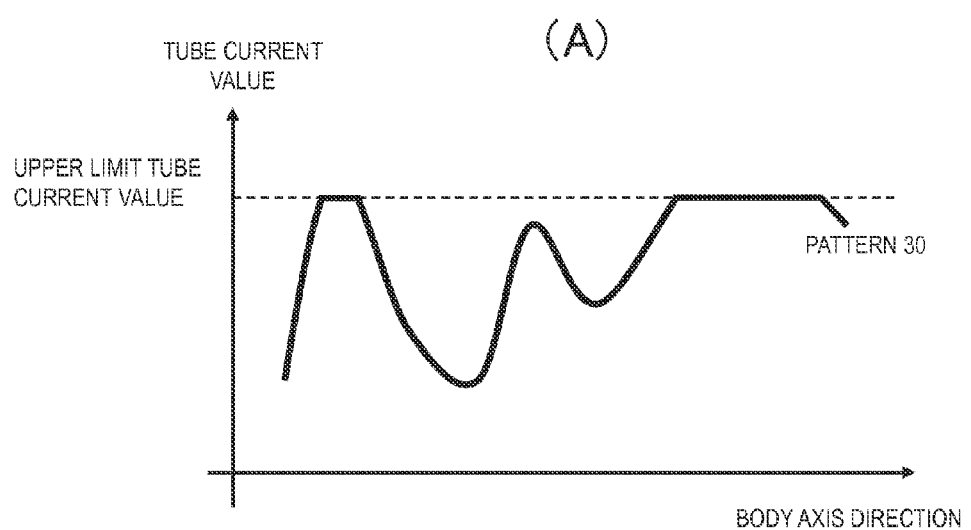
(A)
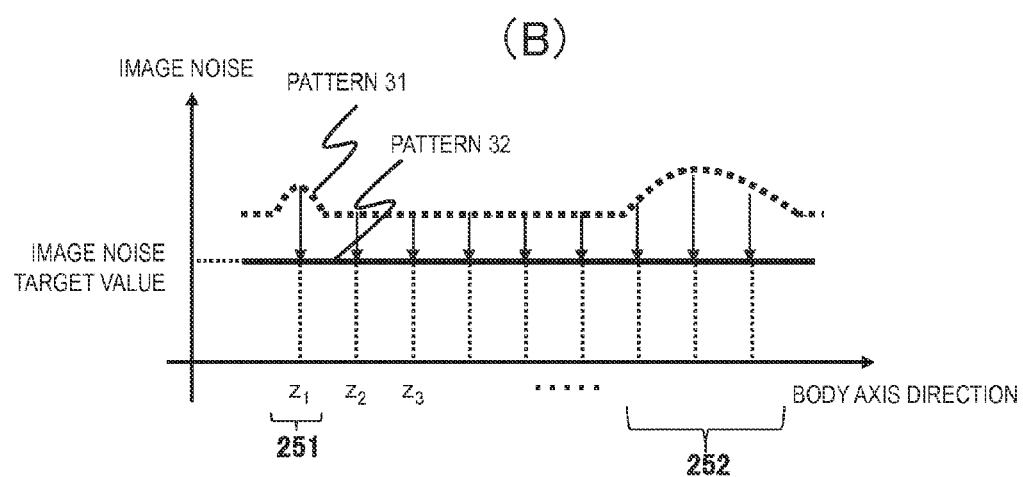
(B)

FIG.29
(A)
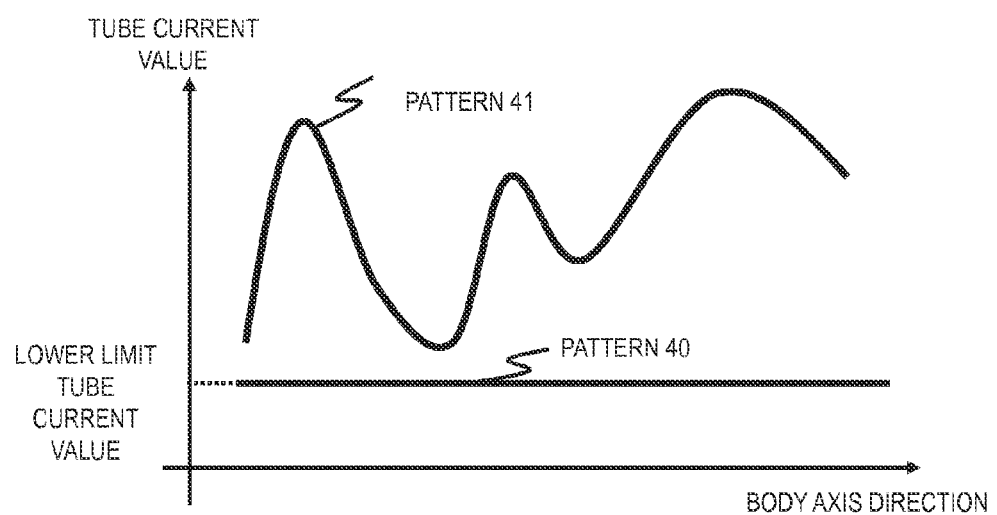
(B)
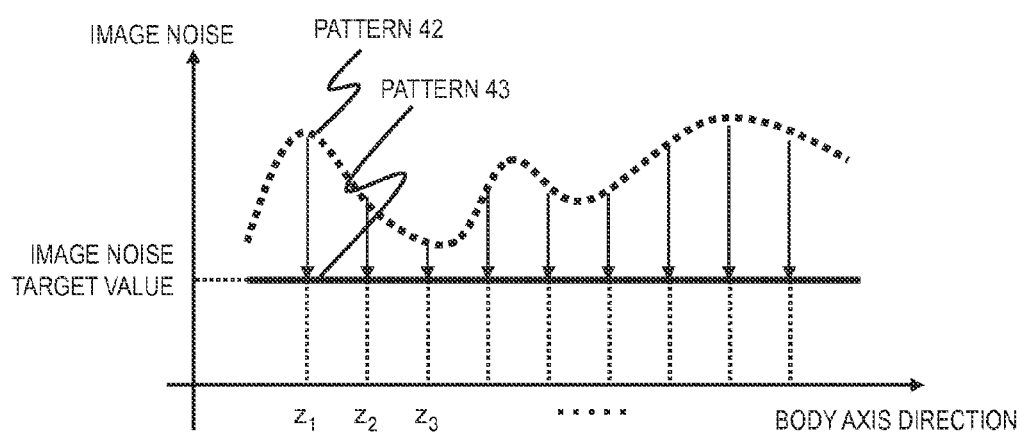

X-RAY CT APPARATUS AND TOMOGRAPHY METHOD

TECHNICAL FIELD

The present invention relates to an X-ray CT apparatus or an X-ray tomography method thereof.

BACKGROUND ART

An X-ray computed tomography (CT) apparatus is intended to reconstruct a tomographic image of an object using projection data from a plurality of angles that is obtained by rotating an X-ray source, which emits X-rays to an object, and an X-ray detector, which detects the amount of X-rays transmitted through the object as projection data, around the object, and display the reconstructed tomographic image. An image displayed in the X-ray CT apparatus is intended to depict, for example, the shape of an organ of the object, and is used for diagnostic scanning.

As a general trend, in the X-ray CT apparatus, there is a trade-off between the exposure dose and the image quality. That is, a tendency that the amount of image noise in the reconstructed image increases and the visibility of a lesion or the like becomes worse when reducing the dose at the time of scanning in order to reduce the exposure dose can be seen. Currently, in the X-ray CT field, there is an "X-ray automatic exposure mechanism" that appropriately controls the exposure dose based on the image quality indicator. As the image quality indicator, a standard deviation (hereinafter, referred to as SD) of image noise or a contrast-to-noise ratio (hereinafter, referred to as CNR) is used. In the following description, a mode using an X-ray automatic exposure mechanism based on image noise that the operator desires (hereinafter, an image noise target value) is referred to as an SD mode, and a mode using an X-ray automatic exposure mechanism based on the CNR that the operator desires (hereinafter, a CNR target value) is referred to as a CNR mode.

CITATION LIST

Patent Literature

[PTL 1] PCT International Publication No. WO2012/033028
[PTL 2] PCT International Publication No. WO2009/069489
[PTL 3] Japanese Patent Application Publication No. 2010-193940

SUMMARY OF INVENTION

Technical Problem

As an example of the X-ray CT apparatus including an X-ray automatic exposure mechanism, the X-ray CT apparatus disclosed in PTL 1 is described. In the X-ray CT apparatus disclosed in PTL 1, the tube current value is controlled based on the image noise target value or the CNR target value. However, there is no mention of image quality improvement by the successive approximation process in the image reconstruction.

As described above, in general, the exposure dose tends to increase when trying to improve the image quality of the reconstructed image. It is desirable to suppress the degradation of the image quality of the reconstructed image as much as possible while reducing the exposure dose of the X-ray CT apparatus as much as possible. In this regard, for example, even in the case of PTL 1, further improvement is desired.

It is a purpose of the present invention to provide an X-ray CT apparatus with little image quality degradation even though the tube current value of an X-ray tube relevant to the exposure dose of the X-ray CT apparatus is suppressed.

Solution to Problem

In order to achieve the aforementioned purpose, an X-ray CT apparatus of the present invention includes: an X-ray source that includes an X-ray tube and emits X-rays to an object; an X-ray detector that detects transmitted X-rays that have been emitted from the X-ray source and transmitted through the object; a rotation mechanism in which the X-ray source and the X-ray detector are mounted and which rotates around the object; a system controller that calculates a tube current value of the X-ray tube based on a successive approximation process condition selected from a plurality of successive approximation process conditions and input a scanning condition and/or a reconstruction condition and that performs scanning based on the calculated tube current value of the X-ray tube; and an image reconstruction device that reconstructs a tomographic image of the object, based on the selected successive approximation process condition and the reconstruction condition, from an amount of transmitted X-rays detected by the X-ray detector after being emitted from the X-ray source to the object based on the calculated tube current value of the X-ray tube and being transmitted through the object.

In addition, in order to achieve the aforementioned purpose, there is provided a tomography method of an X-ray CT apparatus according to the present invention including: an X-ray source that includes an X-ray tube and emits X-rays to an object; an X-ray detector that detects transmitted X-rays that have been emitted from the X-ray source and transmitted through the object; a rotation mechanism in which the X-ray source and the X-ray detector are mounted and which rotates around the object; a system controller that performs scanning; and an image reconstruction device that reconstructs a tomographic image of the object from an amount of transmitted X-rays detected by the X-ray detector. The tomography method includes: a first step in which a successive approximation process condition selected from a plurality of successive approximation process conditions is input to the system controller; a second step in which a scanning condition and a reconstruction condition are further input to the system controller; a third step in which the system controller calculates a tube current value of the X-ray tube based on the selected successive approximation process condition and the input scanning condition and/or the reconstruction condition; a fourth step in which the system controller performs scanning based on the calculated tube current value of the X-ray tube; and a fifth step in which the image reconstruction device reconstructs a tomographic image of the object, based on the selected successive approximation process condition and the reconstruction condition, from an amount of transmitted X-rays detected by the X-ray detector after being emitted from the X-ray source to the object based on the tube current value and being transmitted through the object.

Advantageous Effects of Invention

According to the present invention, it is possible to provide an X-ray CT apparatus with little image quality degradation even though the tube current value of an X-ray tube is suppressed.

BRIEF DESCRIPTION OF DRAWINGS

FIG. 3 is a diagram for explaining the flow of the process in the first embodiment.

FIG. 4 is display examples of an input screen in S303 and a numerical table in S306 in FIG. 3 of the first embodiment.

FIG. 5 is a selection screen to select the successive approximation process type in S304 in FIG. 3 of the first embodiment.

FIG. 18 is a display example of a numerical comparison table for comparing the setting conditions and the recommended condition in the second embodiment.

FIG. 19 is a diagram for explaining (2) recommended condition in FIG. 18 of the second embodiment.

FIG. 20 is a diagram for explaining (3) recommended condition in FIG. 18 of the second embodiment.

FIG. 24 is an example of the setting screen for setting the recommended level in the fourth embodiment in advance.

FIG. 26 is a tube current value graph and a predicted image noise value graph for explaining the process of S335 in FIG. 25 of the fifth embodiment.

FIG. 29 is a tube current value graph and a predicted image noise value graph for explaining the process of S345 in FIG. 28 of the sixth embodiment.

DESCRIPTION OF EMBODIMENTS

Figure 1:
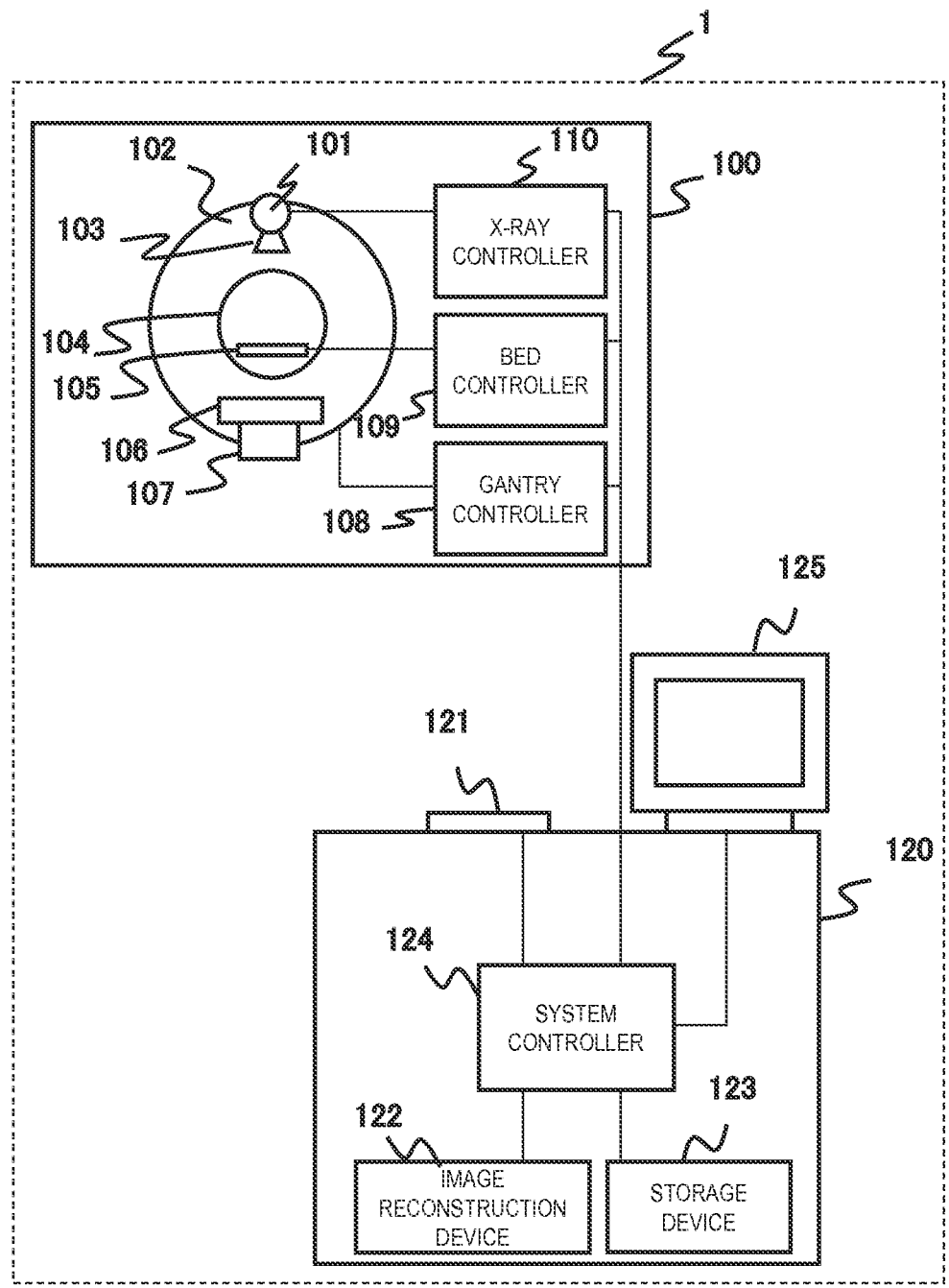
FIG. 1 is a block diagram for explaining the overall configuration according to one embodiment of the present invention.

Hereinafter, an embodiment according to the present invention will be described with reference to the diagrams.
First Embodiment FIG. 1 is a diagram showing the overall configuration of an X-ray CT apparatus 1 that is an embodiment. The X-ray CT apparatus 1 includes a scan gantry unit 100 and a console 120.

The scan gantry unit 100 includes an X-ray tube 101, a rotary disk 102, a collimator 103, an X-ray detector 106, a data collection device 107, a bed 105, a gantry controller 108, a bed controller 109, and an X-ray controller 110. The X-ray tube 101 is a device for irradiating an object placed on the bed 105 with X-rays. The collimator 103 includes a mechanism for limiting the emission range of X-rays emitted from the X-ray tube 101 or an X-ray compensation filter for adjusting the dose distribution of X-rays. The rotary disk 102 includes an opening 104 through which the object placed on the bed 105 is inserted and also includes the X-ray tube 101, the X-ray detector 106, and the data collection device 107 mounted therein, and rotates around the object. The rotary disk 102 serves as a rotation mechanism for rotating the X-ray tube 101, the X-ray detector 106, or the data collection device 107 around the object.

The X-ray detector 106 is a device that is disposed opposite to the X-ray tube 101 and measures the spatial distribution of transmitted X-rays by detecting X-rays transmitted through the object. There is an X-ray detector in which a number of X-ray detection elements are arrayed in the rotation direction of the rotary disk 102 or an X-ray detector in which a number of X-ray detection elements are arrayed in a two-dimensional manner of the rotary axis direction (slice direction) and the rotation direction (channel direction) of the rotary disk 102. The data collection device 107 is a device that collects the amount of X-rays detected by the X-ray detector 106 as digital data.

The gantry controller 108 is a device that controls the rotation of the rotary disk 102. The bed controller 109 is a device that controls the up and down, back and forth, and left and right movement of the bed 105. The X-ray control device 110 is a device that controls electric power supplied to the X-ray tube 101, and can control the tube voltage or the tube current value supplied to the X-ray tube 101.

The console 120 includes an input device 121, an image reconstruction device 122, a display device 125, a storage device 123, and a system controller 124. The input device 121 is a device for inputting required information, such as an object name, examination date and time, and a scanning condition. Specifically, the input device 121 includes a keyboard, a pointing device, or the like. The image reconstruction device 122 is a device that reconstructs a CT image by performing arithmetic processing of the measurement data transmitted from the data collection device 107.

The display device 125 is a device that displays the CT image reconstructed by the image reconstruction device 122. Specifically, the display device 125 is a cathode-ray tube (CRT), a liquid crystal display, or the like. The storage device 123 is a device in which the data collected by the data collection device 107 and image data of the CT image created by the image reconstruction device 122 are stored. Specifically, the storage device 123 is a hard disk drive (HDD) or the like. The system controller 124 is a device that controls these devices, the gantry controller 108, the bed controller 109, and the X-ray controller 110.

The X-ray controller 110 controls electric power input to the X-ray tube 101 based on the scanning condition input through the input device 121, in particular, based on the X-ray tube voltage, X-ray tube current value, and the like, so that the X-ray tube 101 emits X-rays to the object according to the scanning condition. The X-ray detector 106 detects X-rays, which are emitted from the X-ray tube 101 and are transmitted through the object, using a number of X-ray detection elements, thereby measuring the distribution of transmitted X-rays. The rotary disk 102 is controlled by the gantry controller 108, and rotates based on the scanning condition input through the input device 121, in particular, based on the rotation speed or the like. The bed 105 is controlled by the bed controller 109, and operates based on the scanning condition input through the input device 121, in particular, based on the helical pitch or the like.

X-ray emission from the X-ray tube 101 and measurement of the transmitted X-ray distribution by the X-ray detector 106 are repeated while the rotary disk 102 is rotating. As a result, projection data from various angles is acquired. The acquired projection data from various angles is transmitted to the image reconstruction device 122. The image reconstruction device 122 reconstructs a CT image by performing back projection processing on the transmitted projection data from various angles. The CT image obtained by reconstruction is displayed on the display device 125.

Figure 2:
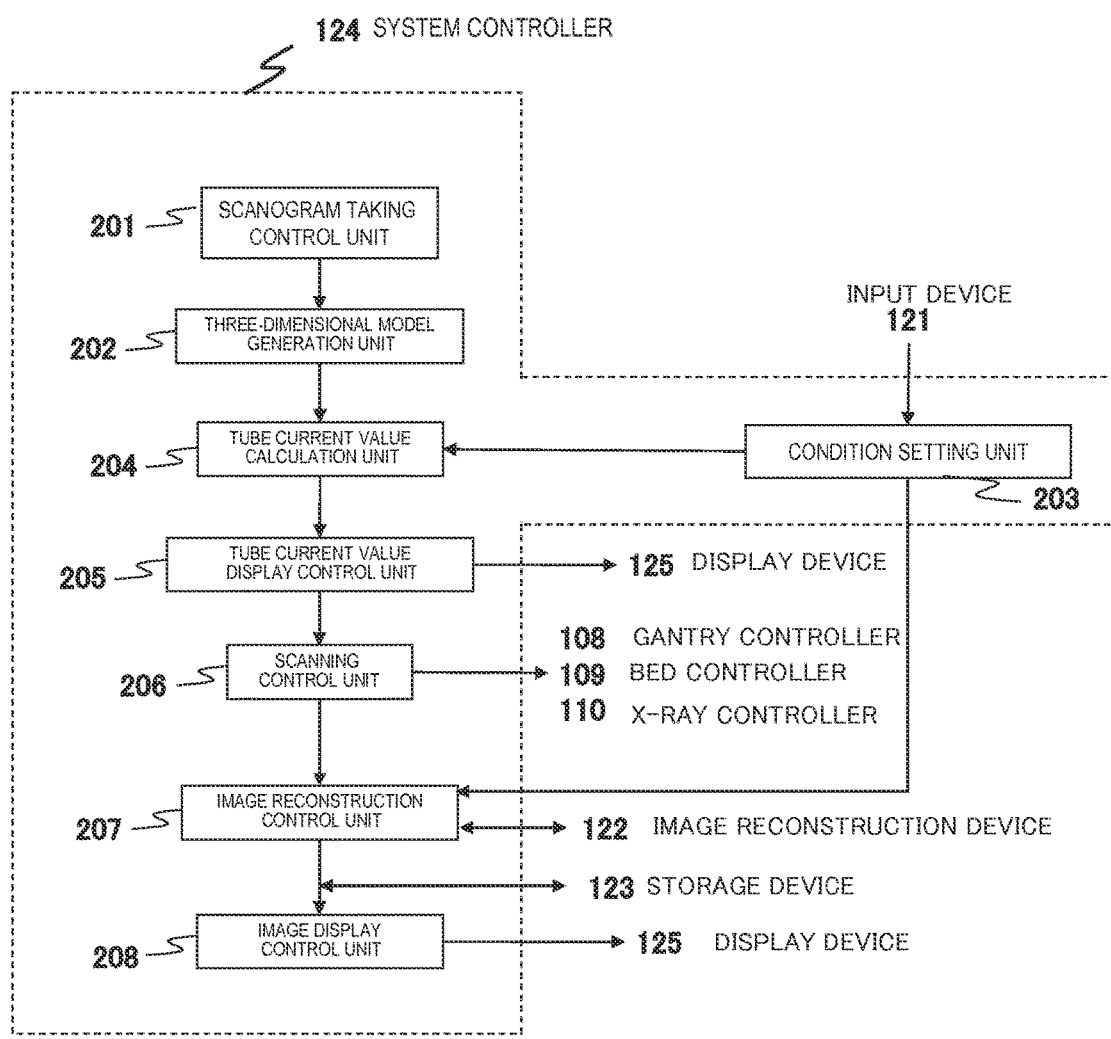
FIG. 2 is a functional block diagram showing the function of a system controller in FIG. 1.

FIG. 2 is a functional block diagram showing the function of the system controller 124 described in FIG. 1. Each unit shown in FIG. 2 is implemented as a function of the system controller 124.

The system controller 124 includes a scanogram taking control unit 201, a three-dimensional model generation unit 202, a condition setting unit 203, a tube current value calculation unit 204, a tube current value display control unit 205, a scanning control unit 206, an image reconstruction control unit 207, and an image display control unit 208.

The scanogram taking control unit 201 controls the scanning of a positioning image (hereinafter, a scanogram), and transmits projection data or image data of the scanogram to the three-dimensional model generation unit 202. The three-dimensional model generation unit 202 generates a cross-section model or a three-dimensional model of the object by analyzing the projection data or image data of the scanogram transmitted from the scanogram taking control unit 201, and transmits the data of the cross-section model or the three-dimensional model to the tube current value calculation unit 204. The condition setting unit 203 sets setting conditions regarding scanning, which are input by the operator using the input device 121 when necessary, and/or setting conditions regarding image reconstruction input when necessary (hereinafter, these setting conditions are referred to as parameters). Parameters relevant to scanning of the setting conditions are transmitted to the tube current value calculation unit 204, and parameters relevant to image reconstruction are transmitted to the image reconstruction control unit 207.

The tube current value calculation unit 204 calculates an appropriate X-ray tube current value along the body axis direction and the rotation direction, in consideration of the effect of the successive approximation process, based on the data of the cross-section model or the three-dimensional model transmitted from the three-dimensional model generation unit 202 and the parameters relevant to scanning and/or image reconstruction transmitted from the condition setting unit 203, and transmits the calculated tube current value to the tube current value display control unit 205. The tube current value display control unit 205 displays the tube current value transmitted from the tube current value calculation unit 204 on the display device 125, and transmits the tube current value to the scanning control unit 206.

The scanning control unit 206 performs scanning according to the tube current value calculated by the tube current value calculation unit 204 while controlling the tube current value in the body axis direction and the rotation direction through the gantry controller 108, the bed controller 109, and the X-ray controller 110. The image reconstruction control unit 207 reconstructs an object tomographic image by controlling the image reconstruction device 122 based on the parameters relevant to image reconstruction transmitted from the condition setting unit 203 and the projection data obtained by scanning, and stores the reconstructed image in the storage device 123 and transmits the reconstructed image to the image display control unit 208. The image display control unit 208 displays the reconstructed image on the display device 125.

FIG. 3 is a flowchart showing the operation according to the first embodiment of the present invention. In step S301, scanogram scanning of an object is performed. In step S302, a three-dimensional model of an object is calculated using the projection data or image data of the scanogram. In addition, optical image capturing or height and weight measurement of an object may be performed in step S301, and a three-dimensional model of an object may be calculated using the optical image or the height and weight in step S302. In step S303, the operator inputs setting conditions regarding scanning or setting conditions regarding image reconstruction onto the display screen of the display device 125 through the input device 121.

As the setting conditions regarding scanning, an image noise target value or a CNR target value, an upper threshold value of a tube current value (hereinafter, referred to as an upper limit tube current value), a lower threshold value of a tube current value (hereinafter, referred to as a lower limit tube current value), a tube voltage, X-ray collimation, helical pitch, rotation speed, focal point size, the shape of an X-ray compensation filter, the presence or absence of an X-ray curing filter, a reconstruction function, slice thickness, and the like can be mentioned. "Reference SD" shown in PTL 1 may be set instead of the CNR target value. As the setting conditions regarding image reconstruction, a reconstruction function, a field-of-view size, slice thickness, and the like can be mentioned.

FIG. 4 is an example of an input screen to input parameters to be set in the case of the SD mode and a display screen to display a calculation result. Also in the case of the CNR mode, the same screen as in the case of the SD mode is applied. Since the basic technical idea in the cases of the SD mode and the CNR mode is the same, illustration and specific description of the CNR mode will be omitted, and the case of the SD mode will be described representatively. FIG. 4(A) is an input example of a screen 300 when the operator inputs setting conditions in steps S303 and S304, and FIG. 4(B) is the screen 300 that displays a result calculated based on the setting conditions input by the operator.

The operator inputs an image noise target value, an upper limit tube current value, a lower limit tube current value, and a successive approximation process level to be described later to an input area 310 using the screen in FIG. 4(A). For example, as shown in FIG. 4(A), the image noise target value of 10.0 (HU), the upper limit tube current value of 500 (mA), the lower limit tube current value of 100 (mA), and the successive approximation process level of 5 ($L_5$) to be described later are input through a pointing device or a keyboard. These may also be input by selection from a pull-down list of values.

When the input numerical values need to be changed, it is possible to place a cursor on the numerical value of each column to be changed and delete the numerical value with a Delete key or the like or to change the numerical value by re-selecting the pull-down value. Although a confirm display 301 should not necessarily be displayed and used, the operability is improved by displaying the confirm display 301 on the screen as shown in FIG. 4.

In FIG. 1, a pointing device can be used as the input device 121. Examples of the pointing device include a mouse, a touch panel, and the like. In FIG. 1, the input device 121 and the display device 125 are shown at different positions. However, this is just an illustration. For example, when the input device 121 includes a touch panel, the touch panel is disposed on the screen of the display device 125 instead of the position of the input device 121 illustrated. An input position is set by touching a predetermined position of the display screen corresponding to the display shown in FIG. 4. In addition, not only by inputting information from the keyboard provided in the input device 121 but also by manual input on the display screen of the display device 125, it is possible to input required information, such as numerical values, through the touch panel.

In step S304, the operator inputs an arbitrary type or level selectively from the predetermined condition of the successive approximation process, for example, from a plurality of types or levels regarding the successive approximation process. First, the successive approximation process level will be described.

As levels of the successive approximation process, N levels of, for example, $L_i$ (i=1, 2, ..., N) are prepared, and the level is selected according to the purpose of scanning. The successive approximation process level indicates the strength of the successive approximation process, and it is assumed that the image noise reduction effect becomes high as the successive approximation process level becomes high, that is, as i increases.

In the level 1 ($L_1$) that is the minimum level, the image noise reduction effect is low. In order to obtain the desired image quality in terms of image-to-noise, it is necessary to suppress an image noise increase in the image itself before the application of the successive approximation process by suppressing the reduction in the amount of X-ray emission from the X-ray tube 101. In this case, the exposure reduction effect tends to decrease. However, at a level at which the image noise reduction effect of the successive approximation process is low, it is possible to suppress the degradation of the spatial resolution compared with an image before the application of the successive approximation process, and it is possible to obtain an image in which the edge of the structure is held.

On the other hand, at a level N ($L_N$) that is the maximum level, the image noise reduction effect of the successive approximation process is increased. Accordingly, since it is possible to reduce the amount of X-ray emission from the X-ray tube 101 by the amount of the increase, the exposure reduction effect tends to increase. However, time required for the successive approximation process tends to increase as the successive approximation process level increases. Although the image noise reduction effect increases as the successive approximation process level increases, the spatial resolution of an image is likely to decrease. Accordingly, the edge of the object tends to blur. Therefore, it is desirable to select the successive approximation process level in consideration of the diagnostic purpose, a scanning target, and the like.

In the input operation of step S304, the operator selects an arbitrary level and inputs the arbitrary level to the item of the successive approximation process level of the input area 310 using the screen in FIG. 4(A) displayed on the display device 125.

Next, the successive approximation process type will be described. As will be described later, the tube current value of the X-ray tube 101 is calculated based on the setting conditions input in steps S303 and S304, and there is a plurality of tube current value calculation methods. A plurality of types of the successive approximation process may be made available, so that the operator selects the type of successive approximation process suitable for the diagnostic purpose or the scanning target. FIG. 5 is a selection screen to select the type of successive approximation process. FIG. 5 is a screen that is displayed when a type change display 303 in FIG. 4 is clicked.

Although the details of the tube current value calculation method according to the type of successive approximation process will be described later, for example, there are cases of (1) when the tube current value reduction rate (image noise reduction rate) according to the successive approximation process depends on the tube voltage and the process level, (2) when the tube current value reduction rate (image noise reduction rate) according to the successive approximation process depends on the field-of-view size and the process level, and (3) when the tube current value reduction rate (image noise reduction rate) according to the successive approximation process depends on image noise and the process level. On a selection screen 400 in FIG. 5, the types (1) to (3) described above are displayed. When the confirm display 301 is clicked by clicking the display of the type, the selection of the type of successive approximation process is determined. For example, the selected type is colored or the typeface is changed, so that the selected type is distinguished from other types.

When the selected type needs to be changed, the type change display 303 in FIG. 4 is clicked and the type is re-selected from the selection screen in FIG. 5. A tube current value calculation method suitable for each type of successive approximation process is built into a program in advance, and a tube current value calculation method according to the selected successive approximation process type is automatically selected. Instead of the type change display 303 in FIG. 4 or the selection screen in FIG. 5, an item to select the successive approximation process type may be newly provided in the input area 310 in FIG. 4 so that the successive approximation process type can be selected in a pull-down form or the like. Details of the tube current value calculation method will be described later.

Next, step S305 will be described. Based on the setting conditions regarding scanning, such as the image noise target value (CNR target value in the case of the CNR mode), the upper limit tube current value, and the lower limit tube current value set by the operator in step S303, and the successive approximation process type or level set by the operator in step S304, a "predicted average image noise value" ("predicted average CNR value" in the case of the CNR mode) that is a body axis direction average value of the image noise that is predicted, a "required maximum tube current value" and a "required minimum tube current value" that are maximum and minimum values of the tube current value, and an "average tube current value" that is an average value within the scanning range of the tube current value that can actually be emitted in consideration of the influence of clipping or the like are calculated in step S305. The average tube current value is used for comparison with a case of scanning using a fixed tube current value, and helps to determine an increase or decrease in the level of the tube current value, that is in the exposure dose of the object.

Furthermore, a "tube current value reduction rate" of the average tube current value to the tube current value of the conventional automatic X-ray exposure mechanism, a predicted value of the computed tomography dose index (CTDI) that is an indicator of the exposure dose, a predicted value of "image reconstruction time" that changes depending on the setting conditions or the number of iterations of the successive approximation process, a "breath holding time" of the object that changes depending on the scanning condition, and the like are calculated. The image reconstruction time is an important factor to estimate the length of the examination time required until one object leaves the hospital after entering the hospital and performing scanning and image quantity check. By allowing the operator to estimate the examination time, scheduling for the next object or the like can be smoothly performed.

Next, step S306 will be described. The above-described predicted average image noise value, required maximum tube current value, required minimum tube current value, and average tube current value calculated in step S305 are displayed in an output area 320 of the screen 300 as shown in FIG. 4(B). In addition, the above-described tube current value reduction rate, CTDI, image reconstruction time, and breath holding time are displayed in the output area 320 of the screen 300 in step S306.

Not only the numerical values described above but also the tube current value pattern is displayed on the display device 125. For example, as shown in FIG. 6(A), a scanogram image 1 is displayed so as to be juxtaposed with a tube current value pattern 2 in the body axis direction in the scanning range and a change pattern 3 of the image noise predicted after the application of the successive approximation process (hereinafter, a predicted image noise value) or a change pattern 4 of the CNR predicted after the application of the successive approximation process (hereinafter, a predicted CNR value). In the case of the SD mode, as shown in FIG. 6(B), the set image noise target value and the predicted image noise value pattern 3 are displayed. In the case of the CNR mode, as shown in FIG. 6(C), a CNR target value and the predicted CNR value pattern 4 are displayed.

The scale of a tube current value (mA) is displayed on the upper sides of FIGS. 6(B) and 6(C). For example, the upper limit tube current value is 500 (mA) and the lower limit tube current value is 100 (mA), and each of the values is expressed in a dotted line. The scale of the image noise value and the scale of the CNR value are displayed on the lower sides of FIGS. 6(B) and 6(C), respectively. The image noise target value (for example, 10 HU) is expressed in a dotted line in FIG. 6(B), and the CNR target value is expressed in a dotted line in FIG. 6(C).

The display device 125 may juxtapose these, or may display only the tube current value pattern 2. Instead of the predicted image noise value pattern 3, a change pattern of a value obtained by dividing the predicted image noise value by the image noise target value or a change pattern of the error of the predicted image noise value with respect to the image noise target value maybe displayed. Instead of the predicted CNR value pattern 4, a change pattern of a value obtained by dividing the predicted CNR value by the CNR target value or a change pattern of the error of the predicted CNR value with respect to the CNR target value may be displayed. By displaying the graph of FIG. 6(B) or the graph of FIG. 6(C) so as to be contrasted with the image of the scanogram in FIG. 6(A) as described above, there is an effect that it is easily checked whether or not a tube current value I corresponding to each part of the object is appropriate (for example, the presence or absence of clipping to be described later is easily checked).

Figure 7:
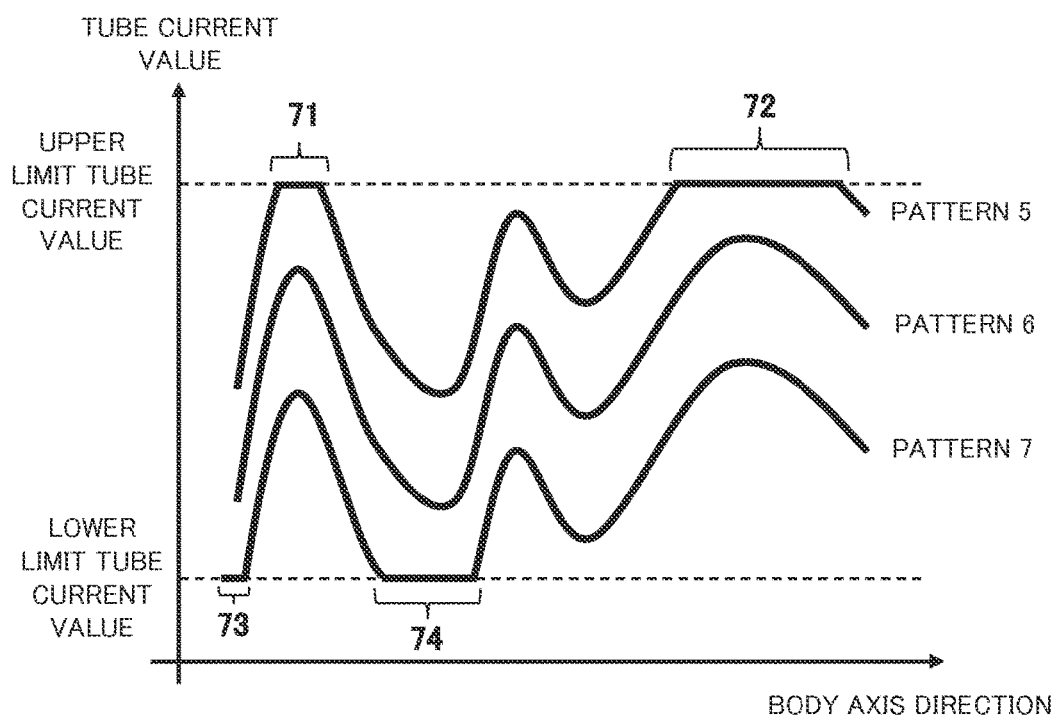
FIG. 7 is a diagram for explaining the clipping of the tube current value.

Here, clipping may occur in which the tube current value I is rounded to the upper limit tube current value when the tube current value I calculated in step S305 exceeds the upper limit tube current value set by the operator in step S303 and the tube current value I is rounded to the lower limit tube current value when the tube current value I calculated in step S305 is less than the lower limit tube current value set by the operator in step S303. FIG. 7 is a tube current value graph in the body axis direction for explaining the clipping.

In FIG. 7, one of the axes of the graph is the body axis of an object, and the other axis is the calculation result of the tube current value of the X-ray tube 101. A tube current value pattern 5 is an example when clipping due to the upper limit tube current value occurs, a tube current value pattern 6 is an example when clipping does not occur, and a tube current value pattern 7 is an example when clipping due to the lower limit tube current value occurs. Each of the graphs shown in the tube current value patterns 5, 6, and 7 is an example of the tube current value pattern 2 in FIG. 6(B) or FIG. 6(C).

When scanning a large object or when scanning a part with large X-ray attenuation, such as a shoulder or a pelvis, a high tube current value is required in order to maintain the image quality. Accordingly, clipping (71, 72) due to the upper limit tube current value, such as the tube current value pattern 5, is likely to occur. When the clipping (71, 72) due to the upper limit tube current value occurs, emission of only a tube current value lower than the required tube current value is possible. As a result, since the image noise becomes higher than the image noise target value or the CNR becomes lower than the CNR target value, it is not possible to achieve the image noise target value or the CNR target value.

When clipping (73, 74) due to the lower limit tube current value, such as the tube current value pattern 7, occurs, the amount of X-rays to be emitted becomes larger than the required amount. As a result, the exposure dose with respect to the object is increased.

By displaying the graphs shown in the tube current value patterns 5, 6, and 7 on the tube current value pattern 2 in FIG. 6(B) or 6(C), the operator can visually check whether or not the clipping has occurred at a glance. Therefore, it is possible to easily determine whether or not it is necessary to review the setting conditions.

Figure 6:
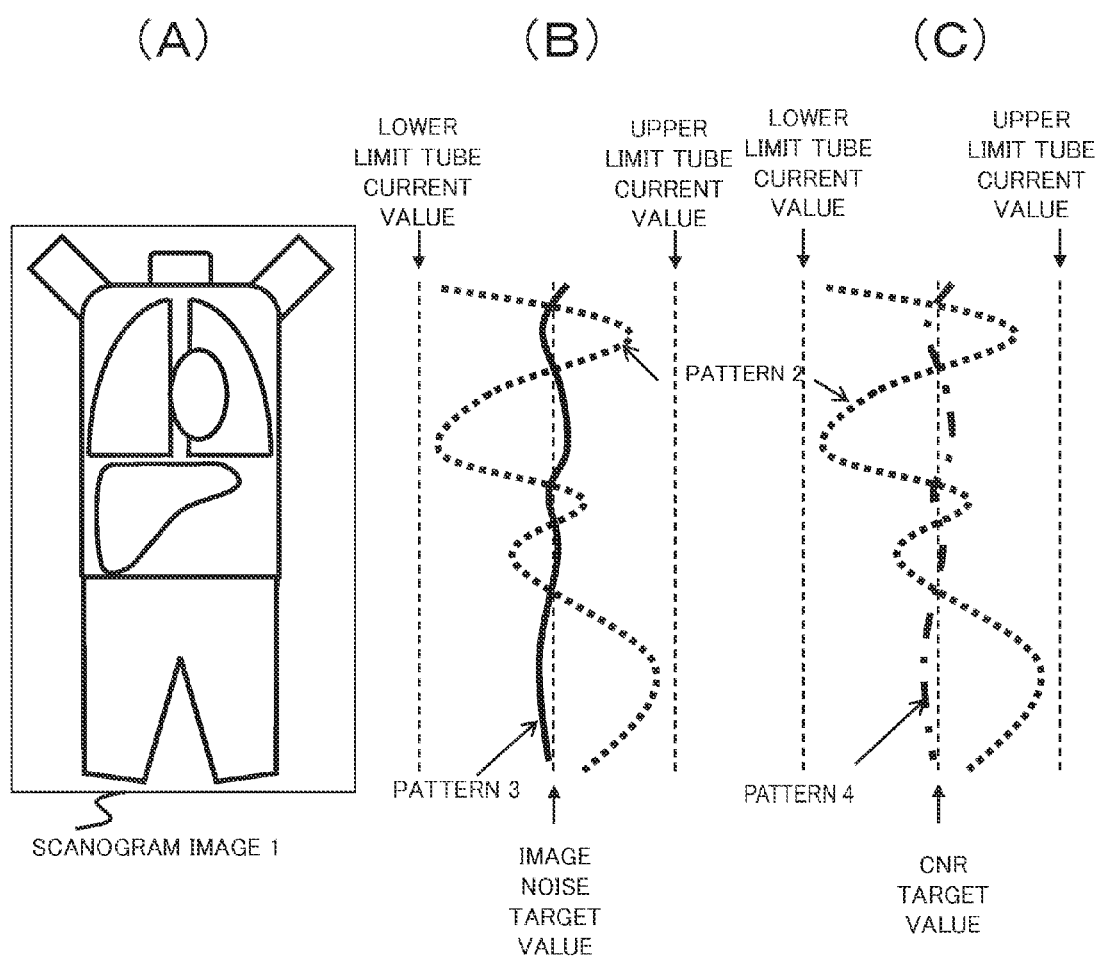
FIG. 6 is a display example of S306 in FIG. 3 of the first embodiment.

A numerical table (FIG. 4) describing the numerical information described above may be displayed on the display device 125 together with the graph shown in FIG. 6. Through the numerical table in FIG. 4(B), it is possible to understand numerically that clipping has occurred when the required maximum tube current value exceeds the upper limit tube current value or when the required minimum tube current value is less than the lower limit tube current value. From the above, the operator can understand the setting conditions quantitatively, and this can be used for the determination of the setting conditions.

Next, step S307 will be described. In step S307, whether or not the balance of the tube current value, the predicted image noise value or the predicted CNR value, and the image noise target value or the CNR target value is appropriate, for example, whether or not to allow the clipping of the tube current value when the clipping of the tube current value has occurred is determined from the information displayed on the display device 125 by the operator. When it is determined that the clipping is not allowed (NG), the process proceeds to step S308. When it is determined that the clipping is allowed (OK), the process proceeds to step S309. When it is determined that the clipping is allowed (OK), the confirm display 301 in FIG. 4 is clicked to confirm the entry. The successive approximation process level selected at that time is set, that is, confirmed. The confirmed successive approximation process level is used in the calculation processing in step S310 to be described later.

Next, step S308 will be described. The operator returns to step S303 or step S304 to reset the tube current value, the predicted image noise value or the predicted CNR value, and the image noise target value or the CNR target value by changing the set numerical values so that the balance of the tube current value, the predicted image noise value or the predicted CNR value, and the image noise target value or the CNR target value is appropriate. When the successive approximation process condition needs to be changed (YES), the process returns to S304. When other setting conditions need to be changed (NO), the process returns to S303. For example, when clipping due to the upper limit tube current value occurs, it is preferable to select the successive approximation process of a higher level or to set a higher image noise target value or a lower CNR target value in order to lower the required tube current. It is preferable to set the upper limit tube current value to a higher value if this is possible.

Resetting of the numerical value in step S303 or S304 can be changed, for example, by placing a cursor on the numerical value to be changed in the input area 310 displayed in FIG. 4(B) and deleting the numerical value with a Delete key or the like and re-inputting a numerical value.

In step S309, scanning at the X-ray tube current value I is performed in the body axis direction and the rotation direction according to the tube current value I calculated in step S305.

In step S310, image reconstruction processing is performed according to the setting conditions regarding the image reconstruction set in step S303 and the successive approximation process set condition in step S304. Image reconstruction methods mainly include a reconstruction method called a reconstruction method of applying successive approximation (hereinafter, a successive approximation application method) and a successive approximation reconstruction method. In any method, the image noise reduction effect can be obtained by performing an iterative process in the course of image reconstruction.

The successive approximation application method can be classified into three types of a successive approximation application method to perform an iterative process in the projection space, a successive approximation application method to perform an iterative process in the image space, and a successive approximation application method to perform an iterative process in the projection space and the image space. For example, in the successive approximation application method to perform an iterative process in the projection space, image data is obtained by performing smoothing processing on projection data repeatedly in the projection space and performing back projection of the noise-reduced projection data. In the successive approximation application method to perform an iterative process in the image space, image noise is reduced by repeatedly performing smoothing processing on image data, which is obtained by performing back projection of projection data, in the image space. In the successive approximation application method to perform an iterative process in the projection space and the image space, noise is reduced by performing smoothing processing in both the projection space and the image space.

In all of the three types of successive approximation application methods, back projection is usually performed once. However, in the successive approximation reconstruction method, image noise is reduced by generating an initial image and then repeatedly performing forward projection from image data to projection data and back projection from projection data to image data. Since the forward projection and the back projection are repeated in the successive approximation reconstruction method, processing time is longer than the successive approximation application method. Accordingly, a high-accuracy image noise reduction effect is obtained.

In the present embodiment, the type of the successive approximation process set in step S304 is matched with either of the successive approximation application method or the successive approximation reconstruction method. That is, according to the type of the successive approximation process set in step S304, image reconstruction is performed using either of the successive approximation application method or the successive approximation reconstruction method.

From the above, when applying the successive approximation process, it is possible to provide an image having image noise or the CNR that the operator desires after reducing the exposure dose more than in the conventional X-ray automatic exposure mechanism by using the image noise reduction effect of the successive approximation process.

Detailed operation of step S305 will be described. The image noise reduction rate in the case of applying the successive approximation process may change depending on various setting conditions. Here, it is assumed that an image noise reduction rate P in the case of applying the successive approximation process is measured in advance, for various setting conditions, by phantom scanning.

Figure 8:
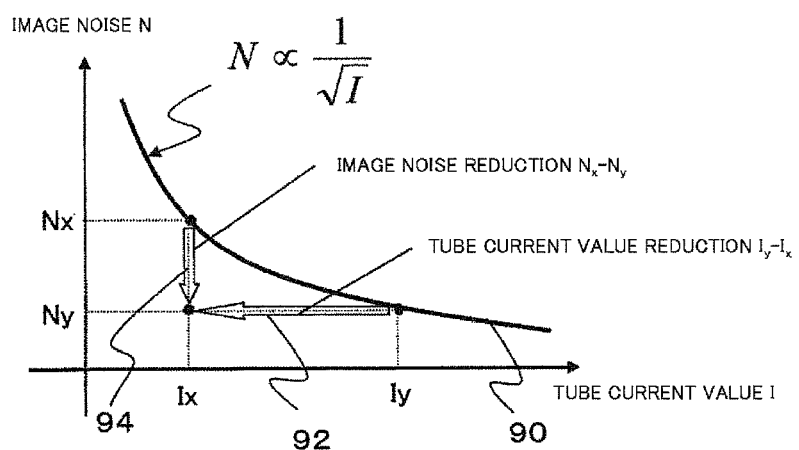
FIG. 8 is a diagram for explaining the image noise reduction rate and the tube current value reduction rate in the case of applying the successive approximation process.

FIG. 8 is a diagram for explaining the image noise reduction rate P and a tube current value reduction rate R in the case of applying the successive approximation process. When the successive approximation process is not applied, the following relational expression is satisfied between the tube current value I and image noise N.

$$N \propto \frac{1}{\sqrt{I}} \quad \text{[Expression 1]}$$

In the expression using a diagram, (Expression 1) is a curve indicated by 90 in FIG. 8. Assuming that image noise before the application of the successive approximation process is Nx and image noise after the application of the successive approximation process is Ny, image noise reduction (Nx−Ny) becomes an arrow 94 shown in FIG. 8. Therefore, the image noise reduction rate P can be calculated as in (Expression 2).

$$P = \frac{Nx - Ny}{Nx} \quad \text{[Expression 2]}$$

When the successive approximation process is not applied, a tube current Ix is required to achieve the image noise Nx, and a tube current Iy (tube current value higher than Ix) is required to achieve the image noise Ny. However, when the successive approximation process is applied, it is possible to achieve the image noise Ny by scanning at the tube current value Ix lower than the tube current value Iy, instead of the tube current value Iy. That is, by applying the successive approximation process, it is possible to perform scanning at a tube current value lower than in the related art in order to achieve the same image noise as in the related art. The reduction of the tube current value (Iy−Ix) is an arrow 92 shown in FIG. 8. Therefore, the tube current value reduction rate R can be calculated as in (Expression 3).

$$P = \frac{Iy - Ix}{Iy} \quad \text{[Expression 3]}$$

By (Expression 1), (Expression 2), and (Expression 3), the tube current value reduction rate R can be written as follows using the image noise reduction rate P.

$$R = 1 - (1-P)^2 \quad \text{[Expression 4]}$$

Although (Expression 4) is the tube current value reduction rate R for acquiring the same image noise value as in the related art, (Expression 4) is also satisfied as the tube current value reduction rate R for acquiring the same CNR as in the related art. The CNR assumed herein is a value obtained by dividing the average CT value difference (hereinafter, contrast) between the identification target and the surrounding tissue by the value of image noise. Since the contrast is not changed before and after the application of the successive approximation process, it is also possible to achieve the same CNR as in the related art if the same value as in the related art can be achieved as the image noise.

As various parameters contributing to the image noise reduction rate, for example, a tube voltage, X-ray collimation, helical pitch, rotation speed, focal point size, the shape of an X-ray compensating filter, the presence or absence of an X-ray curing filter, a reconstruction function, slice thickness, field-of-view size, object size, object position, a projection data value of an object, an integrated value of projection data of an object, and the like can be mentioned.

The field-of-view size, the object size, the object position, the projection data value of an object, and the integrated value of projection data of an object are a number of consecutive values (for example, any of 30 mm to 500 mm in the case of the field-of-view size), while the tube voltage, the X-ray collimation, the helical pitch, the rotation speed, the focal point size, the shape of an X-ray compensating filter, the presence or absence of an X-ray curing filter, the reconstruction function, and the slice thickness are one of a relatively small number of choices (for example, one of four voltages of 80 kV, 100 kV, 120 kV, and 140 kV in the case of the tube voltage). An example of a method for calculating an appropriate tube current value will be described by using the tube voltage as a representative of the former in type 1 and the field-of-view size as a representative of the latter in type 2. In addition, an example of a method for calculating an appropriate tube current value when the image noise reduction rate depends on image noise itself will be described as type 3.

[Type 1: when the image noise reduction effect of the successive approximation process depends on the tube voltage]

Figure 9:
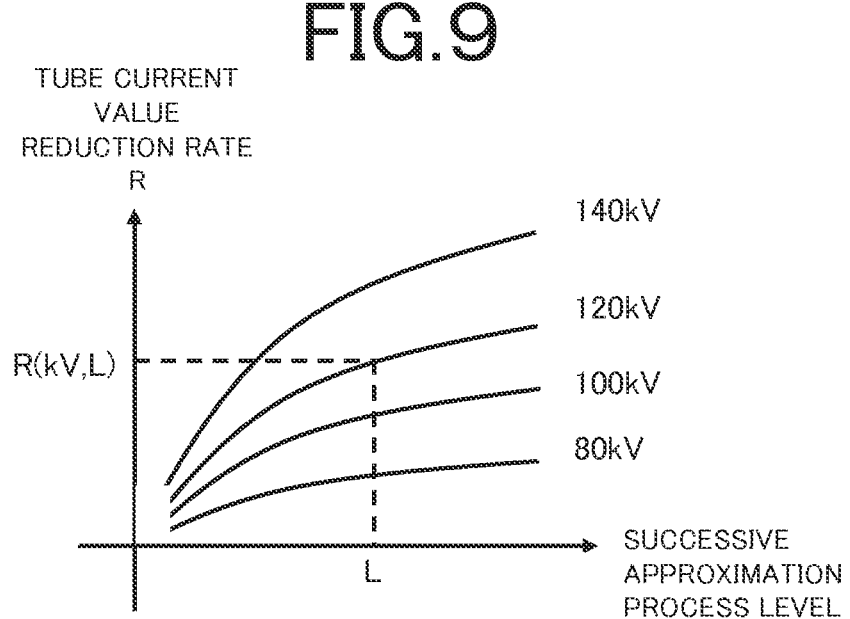
FIG. 9 is a change curve of the tube current value reduction rate according to the tube voltage in S305 in FIG. 3 of the first embodiment.
Figure 10:
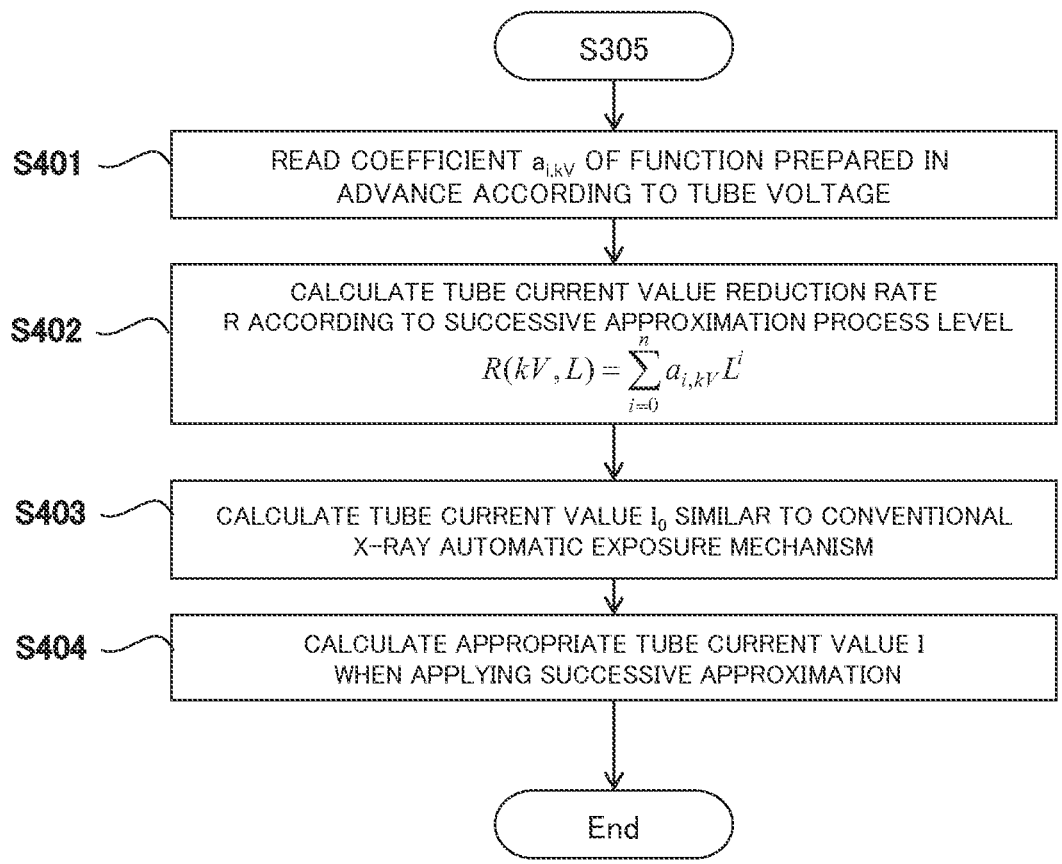
FIG. 10 is a diagram for explaining the flow of the process for calculating an appropriate tube current value according to the tube voltage in S305 in FIG. 3 of the first embodiment.

First, a case where the image noise reduction effect of the successive approximation process depends on the tube voltage will be described. For each tube voltage, an image noise reduction rate for the successive approximation process level is measured, and the tube current value reduction rate R is calculated according to (Expression 4). For example, the tube current value reduction rate R is calculated in advance as an n-th order function of a value L obtained by quantifying the successive approximation process level (FIG. 9). Here, L is not necessarily limited to an integer. In the storage device 123, an n-th order coefficient $a_{i, kv}$ (i=0, 1, 2, . . . , n) of the n-th order function is stored in advance for each tube voltage (kV). FIG. 10 is a flowchart showing the detailed operation of step S305 under such conditions.

In step S401, the system controller 124 reads the coefficient $a_{i, kv}$ (i=0, 1, 2, . . . , n) of the n-th order function from the storage device 123 according to the tube voltage set by the operator in step S303.

Then, in step S402, the tube current value reduction rate R(kV, L) is calculated according to the successive approximation process level L selected by the operator in step S304 in FIG. 3, as shown in (Expression 5). When the successive approximation process is not applied, R(kV, L)=0 is assumed.

$$R(kV, L) = \sum_{i=0}^{n} a_{i,kV} L^i \quad \text{[Expression 5]}$$

In step S403, similarly to the conventional X-ray automatic exposure mechanism, an X-ray tube current value $I_0$ (z, θ) is calculated for each body axis direction (slice position: z) and each rotation direction (X-ray tube phase angle: θ) when the successive approximation process is not taken into consideration.

In step S404, an X-ray tube current value I(z, θ) considering the successive approximation process for each body axis direction and each rotation direction is calculated according to (Expression 6) using the tube current value $I_0$ (z, θ) and the tube current value reduction rate R(kV, L) calculated by (Expression 5).

$$I(z, θ) = (1 - R(kV, L)) \times I_0(z, θ)$$

Although an example in which the tube current value reduction rate R is calculated as a polynomial of the n-th order is shown herein, the function is not limited to the polynomial. In addition, although an example is shown in which the tube current value reduction rate is held as a "function of the successive approximation process level" for each tube voltage, the tube current value reduction rate may be held as a "function of the tube voltage" for each successive approximation process level, or may be held as a matrix of the successive approximation process level and the tube voltage that has a "table form".

From the above, when the image noise reduction effect of the successive approximation process depends on the parameter that takes one of a relatively small number of choices, it is possible to calculate an appropriate tube current value when applying the successive approximation process.

[Type 2: when the image noise reduction effect of the successive approximation process depends on the field-of-view size]

Figure 11:
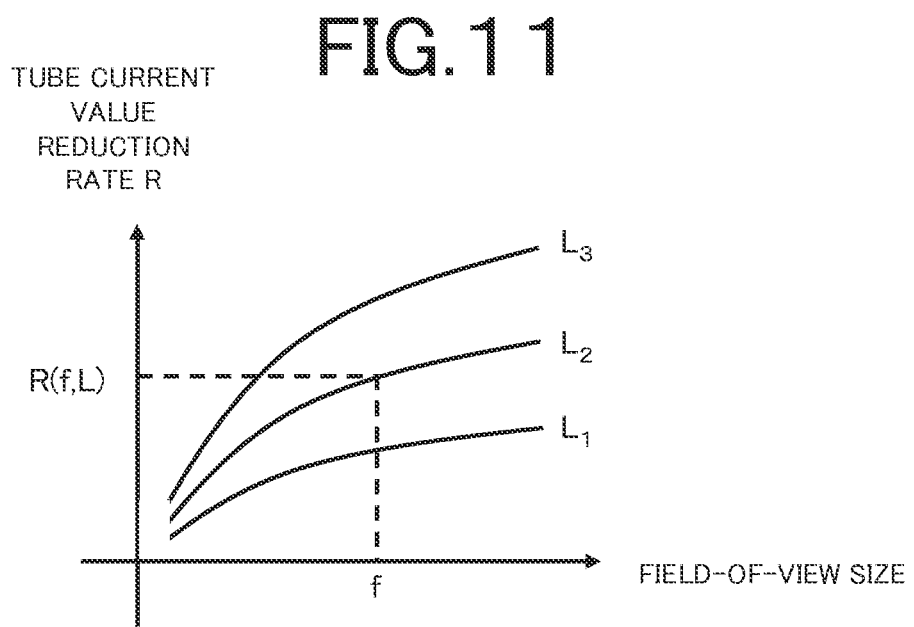
FIG. 11 is a change curve of the tube current value reduction rate according to the field-of-view size in S305 in FIG. 3 of the first embodiment.
Figure 12:
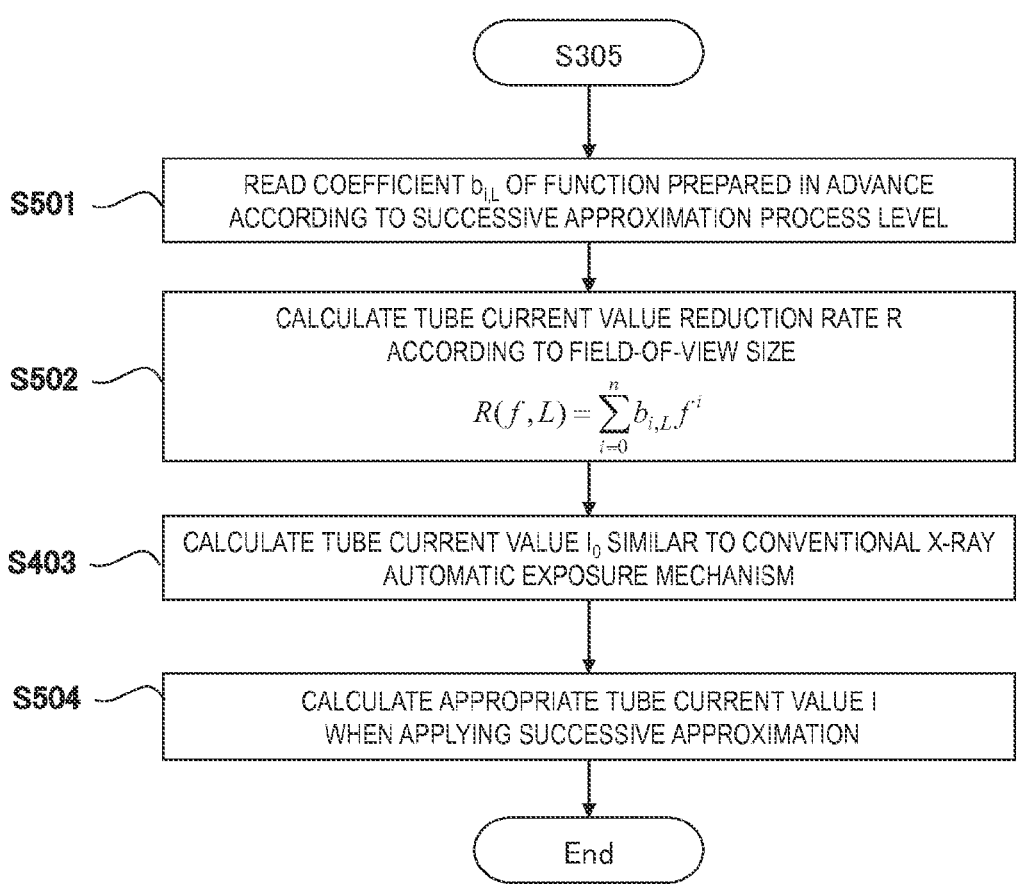
FIG. 12 is a diagram for explaining the flow of the process for calculating an appropriate tube current value according to the field-of-view size in S305 in FIG. 3 of the first embodiment.

Next, a case where the image noise reduction effect of the successive approximation process depends on the field-of-view size will be described. For each successive approximation process level, an image noise reduction rate for the representative field-of-view size is measured, and the tube current value reduction rate R is calculated according to (Expression 4). For example, as shown in FIG. 11, the tube current value reduction rate R is calculated in advance as an n-th order function of a field-of-view size f. In the storage device 123, an n-th order coefficient $b_{i,L}$ (i=0, 1, 2, . . . , n) of the n-th order function is stored in advance for each successive approximation process level (L). FIG. 12 is a diagram showing the detailed operation of step S305 under such conditions.

In step S501, the system controller 124 reads the coefficient $b_{i,L}$ (i=0, 1, 2, . . . , n) of the n-th order function from the storage device 123 according to the successive approximation process level L set by the operator in step S304.

In step S502, a tube current value reduction rate R(f, L) is calculated according to the field-of-view size f set by the operator in step S303, as shown in (Expression 7). When the successive approximation process is not applied, R(f, L)=0 is assumed.

$$R(f, L) = \sum_{i=0}^{n} b_{i,L} f^i \qquad \text{[Expression 7]}$$

Explanation of step S403 will be omitted since the operation content is the same as step S403 in FIG. 10.

In step S504, an X-ray tube current value I(z, θ) considering the successive approximation process for each body axis direction and each rotation direction is calculated according to (Expression 8) using the tube current value $I_0$(z, θ) and the tube current value reduction rate R(f, L) calculated by (Expression 7).

$$I(z,\theta)=(1-R(f,L))\times I_0(z,\theta) \qquad \text{[Expression 8]}$$

From the above, when the image noise reduction effect of the successive approximation process depends on the parameter that takes consecutive values, it is possible to calculate an appropriate tube current value when applying the successive approximation process with high accuracy.

[Type 3: when the image noise reduction effect of the successive approximation process depends on image noise itself]

Next, a case where the image noise reduction effect of the successive approximation process depends on image noise itself will be described. For each successive approximation process level, an image noise reduction rate for the representative image noise is measured, and the tube current value reduction rate R is calculated according to (Expression 4).

Here, it is preferable that the tube current value reduction rate R is held in a system as a function of the image noise Ny after the application of the successive approximation process instead of the image noise Nx before the application of the successive approximation process. When the image noise Nx is reduced to the image noise Ny by the application of the successive approximation process, it can be understood that "in order to obtain an image of the image noise Ny, the tube current value can be reduced by R". The image noise Ny is an image noise to be achieved after the application of the successive approximation process, and corresponds to an image noise target value in the SD mode and to "reference SD" shown in PTL 1 in the CNR mode. If the tube current value reduction rate R is held as a function of the image noise Ny after the application of the successive approximation process so that it can be seen that the tube current value required to achieve the image noise Ny in the conventional X-ray automatic exposure mechanism is $I_0$, it is possible to easily calculate an appropriate tube current value when using the successive approximation process.

Figure 13:
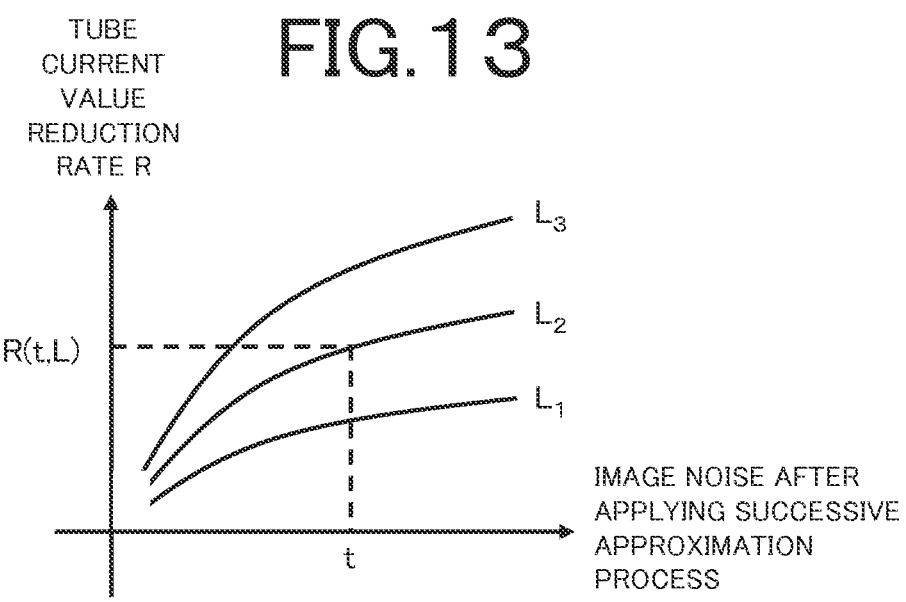
FIG. 13 is a change curve of the tube current value reduction rate according to image noise after the application of the successive approximation process in S305 in FIG. 3 of the first embodiment.
Figure 14:
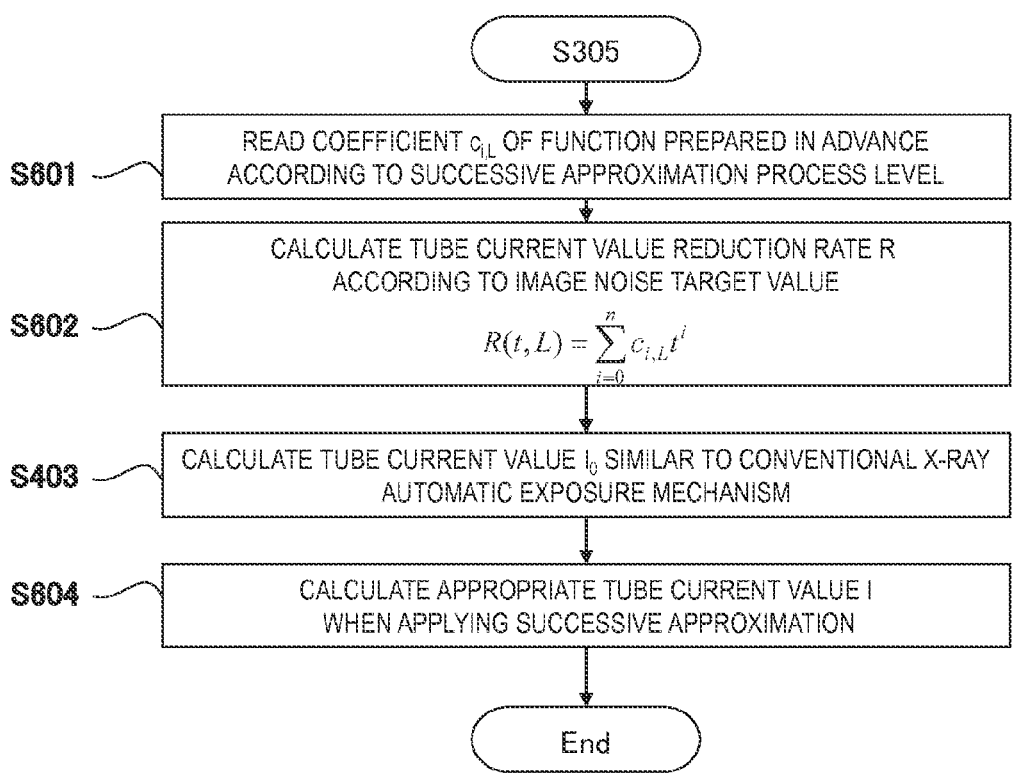
FIG. 14 is a diagram for explaining the flow of the process for calculating an appropriate tube current value according to image noise after the application of the successive approximation process in S305 in FIG. 3 of the first embodiment.

For example, the tube current value reduction rate R is calculated in advance as an n-th order function of image noise t after the application of the successive approximation process (FIG. 13). In the storage device 123, an n-th order coefficient $c_{i,L}$ (i=0, 1, 2, . . . , n) of the n-th order function is stored in advance for each successive approximation process level (L). FIG. 14 is a diagram showing the detailed operation of step S305 under such conditions.

In step S601, the system controller 124 reads the coefficient $c_{i,L}$ (i=0, 1, 2, . . . , n) of the n-th order function from the storage device 123 according to the successive approximation process level L set by the operator in step S304.

In step S602, a tube current value reduction rate R(t, L) is calculated according to the image noise target value or the reference SD set by the operator in step S303, as shown in (Expression 9). When the successive approximation process is not applied, R(t, L)=0 is assumed.

$$R(t, L) = \sum_{i=0}^{n} c_{i,L} t^i \qquad \text{[Expression 9]}$$

Since the operation of step S403 is approximately the same as step S403 of FIG. 10, explanation thereof will be omitted.

In step S604, an X-ray tube current value I(z, θ) considering the successive approximation process for each body axis direction and each rotation direction is calculated according to (Expression 10) using the tube current value $I_0$(z, θ) and the tube current value reduction rate R(t, L) calculated by (Expression 9).

$$I(z, \theta)=(1-R(t, L))\times I_0(z, \theta) \qquad \text{[Expression 10]}$$

By calculating the tube current value reduction rate R as a function of image noise after the application of the successive approximation process instead of image noise before the application of the successive approximation process, it is possible to easily calculate an appropriate tube current value using the value of the reference SD or the image noise target value set during the use of the X-ray automatic exposure mechanism. From the above, when the image noise reduction effect of the successive approximation process depends on the image noise, it is possible to calculate an appropriate tube current value when applying the successive approximation process.

Although the method of calculating an appropriate tube current value using the tube current value reduction rate by the application of the successive approximation process in step S305 has been shown above, it is also possible to calculate an appropriate tube current value using the image noise reduction rate by the application of the successive approximation process. As an example, a method of calculating an appropriate tube current value using the image noise reduction rate in type 1 is shown.

[Another method of type 1: method of calculating an appropriate tube current value using the image noise reduction rate when the image noise reduction effect of the successive approximation process depends on the tube voltage]

Figure 15:
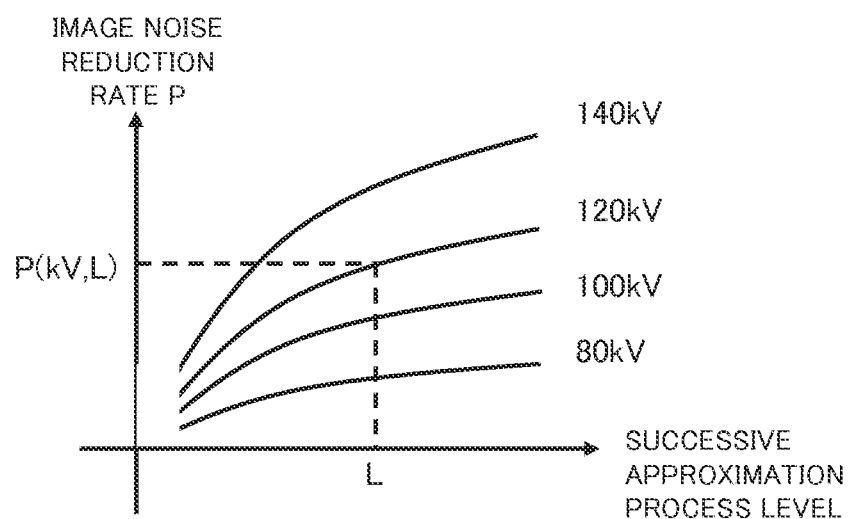
FIG. 15 is a change curve of the image noise reduction rate according to the tube voltage in S305 in FIG. 3 of the first embodiment.
Figure 16:
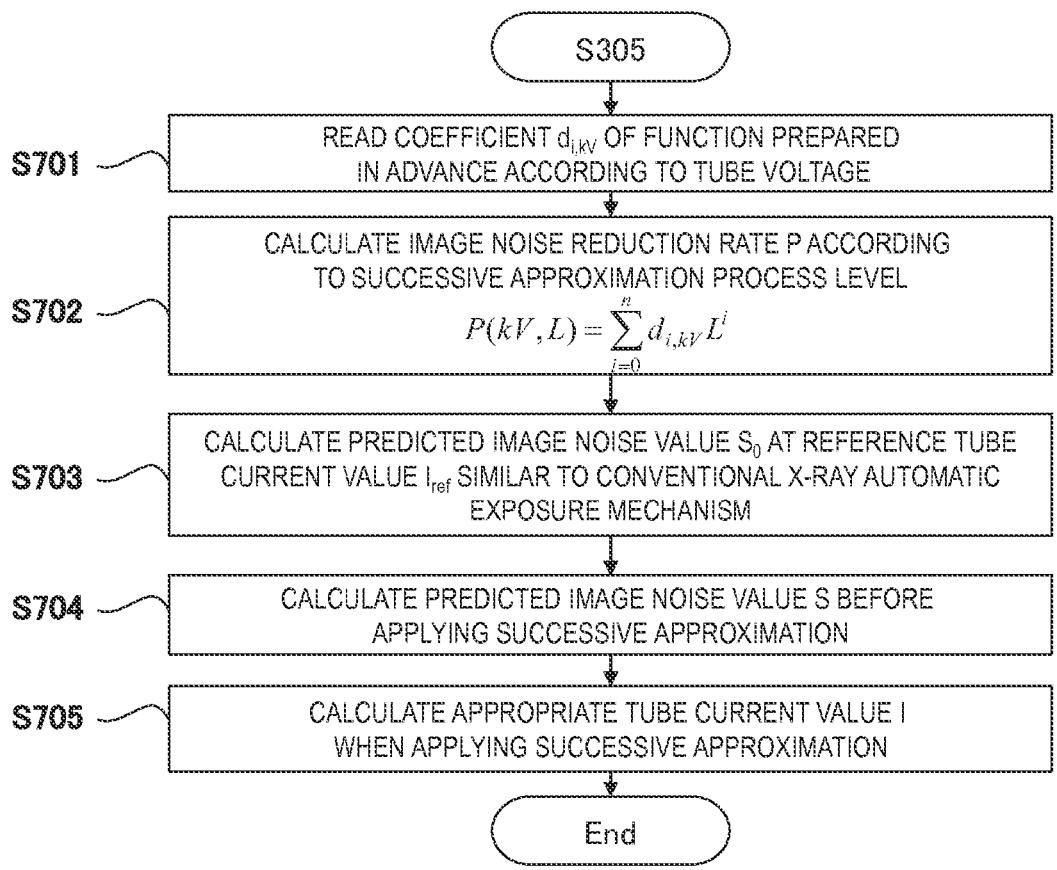
FIG. 16 is a diagram for explaining the flow of the process for calculating an appropriate tube current value according to the tube voltage in S305 in FIG. 3 of the first embodiment using the image noise reduction rate.

For each tube voltage, the image noise reduction rate P for the successive approximation process level is measured. The image noise reduction rate P is calculated in advance as an n-th order function of the value L obtained by quantifying the successive approximation process level (FIG. 15). In the storage device 123, an n-th order coefficient $d_{i,\,kV}$ (i=0, 1, 2, . . . , n) of the n-th order function is stored in advance for each tube voltage (kV). FIG. 16 is a diagram showing the detailed operation of step S305 under such conditions.

In step S701, the system controller 124 reads the coefficient $d_{i,\,kv}$ (i =0, 1, 2, . . . , n) of the n-th order function from the storage device 123 according to the tube voltage set by the operator in step S303.

In step S702, an image noise reduction rate P(kV, L) is calculated according to the successive approximation process level L selected by the operator in step S304, as shown in the following expression. When the successive approximation process is not applied, P(kV, L)=0 is assumed.

$$P(kV, L) = \sum_{i=0}^{n} d_{i,kV} L^i \qquad \text{[Expression 11]}$$

In step S703, similarly to the conventional X-ray automatic exposure mechanism, a predicted image noise value $S_0(z)$ is calculated in the body axis direction at a reference tube current value $I_{ref}$ when the successive approximation process is not taken into consideration.

In step S704, a predicted image noise value S(z) in the body axis direction, which is predicted when the successive approximation process is applied at the reference tube current value $I_{ref}$, is calculated according to the following expression.

$$S(z)=(1-P) \times S_0(z) \qquad \text{[Expression 12]}$$

In step S705, an X-ray tube current value I(z, θ) considering the successive approximation process for each body axis direction and each rotation direction is calculated according to the image noise target value or t that is the reference SD set by the operator in S303, according to the following expression.

$$I(z, \theta) = \qquad \text{[Expression 13]}$$
$$I_{ref} \times \left(\frac{S(z)}{t}\right)^2 \times k \cdot \{(1 + \alpha(z)) + (1 - \alpha(z)) \cdot \cos(\beta \cdot \theta)\}$$

Here, α(z), β, and k are proportionality constants. (Expression 13) is (Expression 5) shown in PTL 2, and is an expression that is often used when calculating the X-ray tube current value I(z, θ) from the predicted image noise value S(z). The method of calculating the X-ray tube current value I(z, θ) is not limited to the method described above, and it is possible to calculate the image noise reduction rate P(kV, L) by (Expression 11) and then calculate the tube current value reduction rate R by (Expression 4) and calculate the X-ray tube current value I(z, θ) from (Expression 6).

As described above, even in the process using the image noise reduction rate by the application of the successive approximation process, it is possible to calculate an appropriate tube current value when applying the successive approximation process.

Second Embodiment

Figure 17:
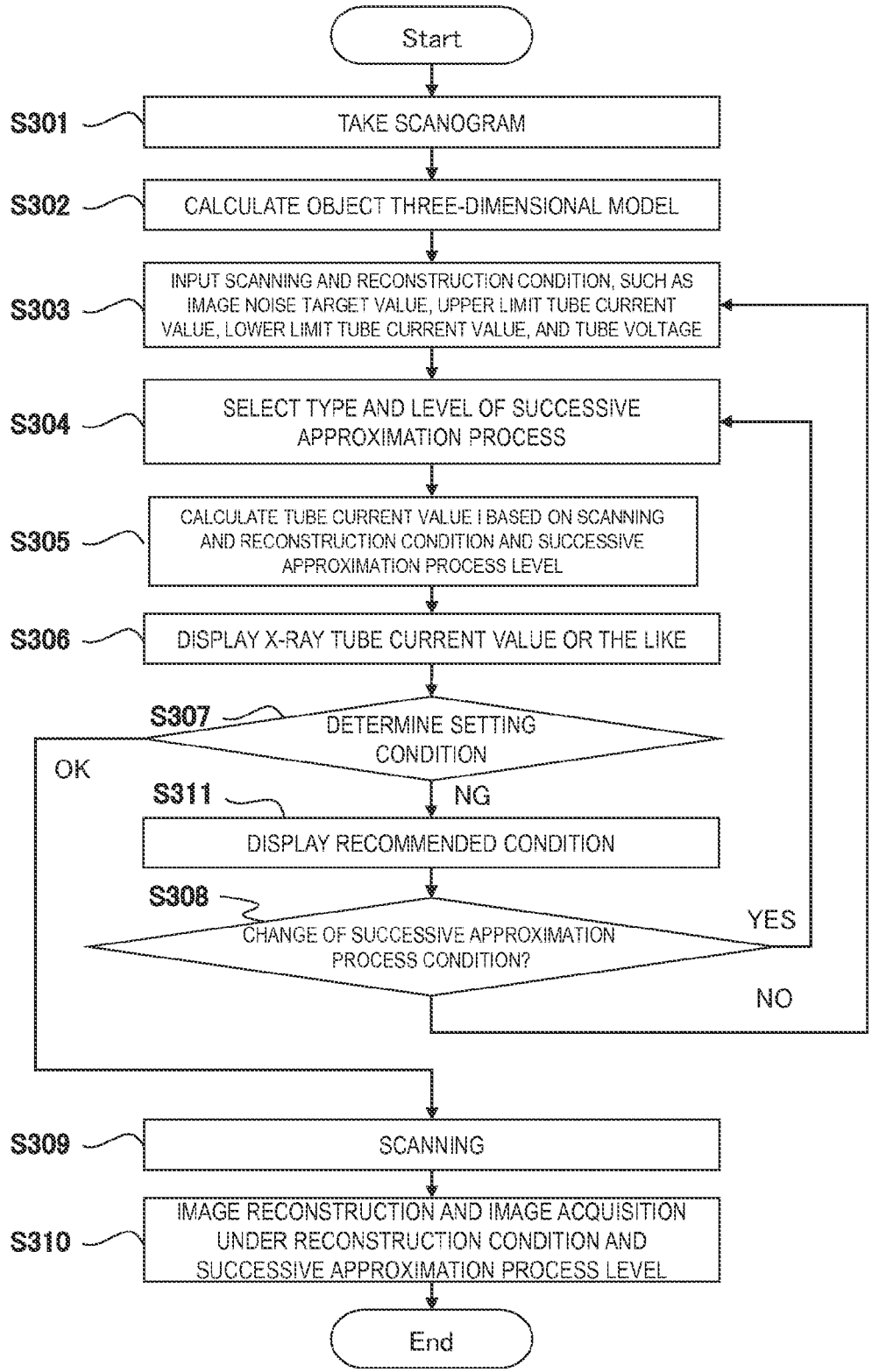
FIG. 17 is a diagram for explaining the flow of the process in a second embodiment.

FIG. 17 is a diagram showing an operation according to a second embodiment of the present invention. Steps denoted by the same reference numerals as in FIG. 3 are approximately the same operations. Differences from the first embodiment shown in FIG. 3 are that a recommended condition is presented to the operator in step S311. As an example, conditions regarding the setting of the successive approximation process level and the setting of the image noise target value will be described as a recommended condition for the SD mode. A recommended condition for the CNR mode can also be similarly set. Hereinafter, step S311 will be described in detail. Since other steps are the same as in FIG. 3, explanation thereof will be omitted.

In step S307 of FIG. 17, it is determined from an input instruction or the like whether or not the current value of the X-ray tube 101 or the like displayed in the previous step S306 is an acceptable value. For example, when the predicted image noise value pattern exceeds the image noise target value, it is preferable to set the upper limit tube current value to a high value or set a higher image noise target value in order to ensure a certain degree of dose. As shown in step S311 of the second embodiment, a recommended condition may be displayed. By presenting the recommended condition in this manner, the operator can set the desirable successive approximation process level more easily or appropriately.

In step S311, a recommended condition, which is useful when resetting the setting conditions for the condition set roughly by the operator, is presented. FIG. 18 is a display example of a numerical comparison table 500 that is presented so that the condition set by the operator and the recommended condition are compared with each other. In the numerical comparison table, information, such as a successive approximation process level, an image noise target value (CNR target value in the case of the CNR mode), a predicted average image noise value (predicted average CNR value in the case of the CNR mode), an upper limit tube current value, a lower limit tube current value, a required maximum tube current value, a required minimum tube current value, an average tube current value, and an image reconstruction time, is displayed so as to be compared with each other. * mark in the numerical comparison table 500 indicates a parameter set by the operator.

When resetting the setting conditions, for example, a "recommended condition" display (not shown) may be given on the screen of FIG. 4(A) together with the "confirm" display 301 and the "type change" display 303 so that the numerical comparison table 500 is displayed when the display is clicked, or the numerical comparison table 500 may be displayed in FIG. 4(A) by default. At the time of resetting, the operator may input the numerical values while observing the numerical comparison table 500, or displays such as "(1) recommended condition input" and "(2) recommended condition input" may be given (not shown) so that the numerical values of the recommended condition are automatically input when these displays are clicked.

(2) recommended condition and (3) recommended condition in FIG. 18 are conditions for avoiding clipping due to the upper limit tube current value when the clipping occurs in (1) setting conditions. (2) Recommended condition is a mode to reduce the tube current value by using the image noise reduction effect of the successive approximation process of level 5, which is higher than the successive approximation process level 3 of setting conditions, while using the same image noise target value 10.0 HU (CNR target value in the case of the CNR mode) as in (1) setting conditions. As shown in FIG. 18, when the recommended condition of (2) is applied, the required maximum tube current value is reduced by about 30% from 670 (mA), which is the setting conditions of (1), to 480 (mA). It can also be seen that the required minimum tube current value is reduced by about 30% from 350 (mA), which is the setting conditions of (1), to 250 (mA). However, since the number of iterations is increased due to using the successive approximation process of high level, the image reconstruction time may be increased. In the present embodiment, as shown in FIG. 18, the image reconstruction time is 30 (s) in (1) setting conditions, but is increased to 50 (s) in (2) setting conditions.

The recommended condition of (3) is a mode to reduce the tube current value by setting the slightly higher image noise target value (or slightly lower CNR target value) while using the same successive approximation process level as in (1) setting conditions. Specifically, as shown in FIG. 18, the image noise target value is set to 10.0 HU in the setting conditions of (1), but is set to the slightly higher target value 11.8 HU in the recommended condition of (3). In the recommended condition of (3), the successive approximation process level is not changed at the same level 3 as in the setting conditions of (1). Accordingly, the image reconstruction time is 30 (s) that is the same as in the setting conditions of (1).

Next, a tube current value pattern and a predicted image noise value pattern (in the case of the SD mode) when the recommended conditions of (2) and (3) are selected will be described with reference to FIGS. 19 and 20 while comparing the patterns with those in the setting conditions of (1). First, a tube current value pattern and a predicted image noise value pattern when the recommended condition of (2) in FIG. 18 is selected will be described with reference to FIG. 19.

In (1) setting conditions in FIG. 18, it is assumed that clipping of the tube current value due to the upper limit tube current value occurs in portions indicated by 181 and 182 in the diagram, as a tube current value pattern 11 in FIG. 19(A). That is, there is a point where the tube current value does not reach the required tube current value in the body axis direction. For this reason, if scanning is performed in this state, a slice where the image noise exceeds the image noise target value occurs in the portions 181 and 182 where the clipping of the tube current value has occurred, as a predicted image noise value pattern 13 in FIG. 19(B). Therefore, in the recommended condition of (2) shown in FIG. 18, the successive approximation process level 5 where it is possible to avoid clipping is applied. By changing the successive approximation process level from the successive approximation process level 3 in (1) setting conditions to the successive approximation process level 5 in (2) setting conditions in FIG. 18, it is possible to make use of the image noise reduction effect of the successive approximation process of higher level. In this manner, an image noise target value, such as a predicted image noise value pattern 14 in FIG. 19(B), can be achieved with a low dose, such as a tube current value pattern 12 in FIG. 19(A). In (2) recommended condition, a typical example is displayed. However, when there is a plurality of applicable successive approximation process levels, a plurality of examples may be displayed.

Next, a tube current value pattern and a predicted image noise value pattern when the recommended condition of (3) in FIG. 18 is selected will be described with reference to FIG. 20. First, as in FIG. 19, the tube current value pattern 11 of (1) setting conditions in FIG. 18 are shown in FIG. 20(A), and the predicted image noise value pattern 13 of (1) setting conditions are shown in FIG. 20(B).

In (3) recommended condition in FIG. 18, an image noise target value (CNR target value in the case of the CNR mode) that can avoid clipping is provided without changing the successive approximation process level. By setting the image noise target value to a slightly higher value (to a slightly lower value in the case of the CNR mode), the required tube current value can be kept low as a tube current value pattern 22, as shown in FIG. 20(A). If scanning is performed in the tube current value pattern 22, image noise becomes a predicted image noise value pattern 24, as shown in FIG. 20(B). Accordingly, a result satisfying the image noise target value set to be slightly higher is obtained. Since fixed image noise is obtained in the body axis direction, it is possible to obtain an image with better image noise uniformity than the predicted image noise value pattern 13.

In addition, obtaining the conventional image noise target value set in (1) setting conditions in FIG. 18 can be realized by a function of redoing the reconstruction (hereinafter, post-reconstruction) by changing the setting conditions regarding ex-post image reconstruction. If the image noise reduction effect of the successive approximation process of a higher level than the level at the time of scanning is used during post-reconstruction, the image noise target value set in (1) can be obtained as a predicted image noise value pattern 25 shown in FIG. 20(B). A recommended level to be used during post-reconstruction and image noise predicted at that time are displayed in the numerical comparison table in FIG. 18.

In addition, as disclosed in PTL 3, clipping may be avoided by resetting, such as reducing the helical pitch or reducing the rotation speed. In this case, however, there is a high possibility that the disadvantage that the breath holding time of the object is increased will occur. If clipping can be avoided just by setting the successive approximation process level, the image noise target value, or the CNR target value as described above, it is possible to obtain a high-quality image without increasing the burden on the object.

By presenting the appropriate recommended condition as described above, the operator can use the recommended condition for the resetting of setting conditions. Even in the conventional scanning condition in which clipping occurs, it is possible to perform scanning to avoid clipping by using the image noise reduction effect of the successive approximation process.

Third Embodiment

Figure 21:
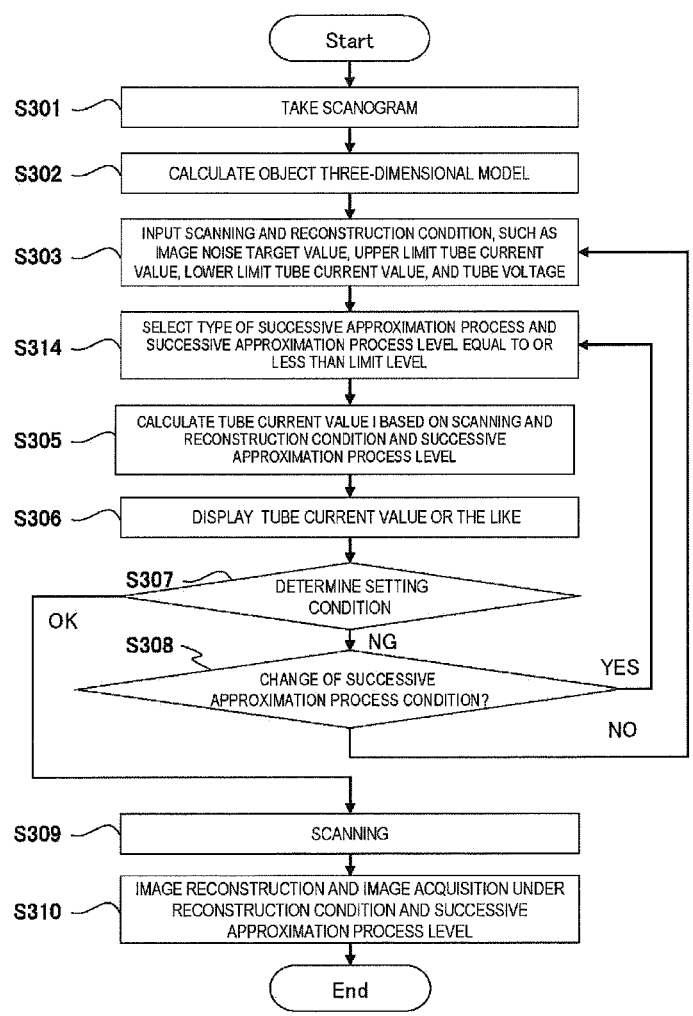
FIG. 21 is a diagram for explaining the flow of the process in a third embodiment.

FIG. 21 is a diagram showing an operation according to a third embodiment of the present invention. Steps denoted by the same reference numerals as in the first embodiment shown in FIG. 3 indicate approximately the same operations. Differences from the first and second embodiments are that the successive approximation process level that can be selected in step S314 is limited in the present embodiment while any successive approximation process level is selected in step S304 in the first and second embodiments. In the second embodiment, a recommended condition is displayed in order to avoid clipping of the tube current, and these are displayed after the tube current value of the X-ray tube is calculated. In the present embodiment, however, the recommended condition is displayed when selecting the successive approximation process level before the tube current value of the X-ray tube is calculated. Hereinafter, it is assumed that N levels of $L_i$ (i=1, 2, . . . , N) are prepared as levels of the successive approximation process and that the image noise reduction effect of the successive approximation process increases as i increases.

When applying the successive approximation process of a high level, the edge of an object tends to blur. In an examination to diagnose an object in which the diameter of an identification target is small and the contrast is low, the visibility of the object may be reduced due to the influence of edge blurring by performing excessive low-dose scanning using the successive approximation process of a high level. Therefore, for example, it is preferable to set a limit value (hereinafter, a limit level) for the successive approximation process level that can be selected according to the examination purpose.

Figure 22:
FIG. 22 is an example of the setting screen for setting the limit level in the third embodiment in advance.

The limit level is registered in advance in the scanning protocol according to the examination purpose. For example, FIG. 22 is a table 600 that shows a limit level for each of apart, tube voltage, and weight. The table 600 may be prepared for each successive approximation process type. As described above, at the level 1 of a minimum level, priority is given to less edge blurring, and an image maintaining the high spatial resolution is obtained. However, the tube exposure reduction effect is reduced. On the other hand, at the maximum level, priority is given to exposure reduction, and it is possible to perform scanning with low exposure. However, the spatial resolution of the image tends to lower.

As shown in the table 600 of the limit level in FIG. 22, when the operator determines to give priority to exposure dose reduction, for example, in the scanning of an object when a part is a lung field and the weight is less than 40 kg, it is possible to perform scanning at any level of level 7 or less by setting the limit level to a high level, such as level 7. In addition, when the operator determines that priority is given to maintaining the image quality rather than to reducing the exposure dose, in order to avoid edge blurring or visibility reduction due to low-dose scanning, in the scanning of an object when a part is abdomen, the tube voltage is 120 kV or more, and the weight is 80 kg or more, it is possible to delete low-dose scanning of level 4 or higher in advance from the choices by setting the limit level to a low level, such as level 3.

The limit level is not limited to a part, a tube voltage, and weight, and may be set using indicators, such as age, BMI, or minimum identification diameters required for diagnosis. For the weight, in the case of equipment in which a weight measurement mechanism is included in a bed or the like, the measured value may be read and used for case classification. If there is a function allowing the registration of the weight of the object at the time of CT examination, the weight may be input using the function so as to be used for case classification. Instead of the weight, cases may be classified according to the size of the three-dimensional model of the object calculated in S302. Hereinafter, step S314 will be specifically described. Since operations in other steps are approximately the same as those in the same steps shown in FIG. 3, explanation thereof will be omitted.

In step S314, an arbitrary successive approximation process level can be selected from only the successive approximation process levels that are equal to or less than the limit level. Specifically, in the input area 310 shown in FIG. 4, only the successive approximation process levels equal to or less than the limit level are provided to the operator in a pull-down form according to the condition set in advance in the table 600, so that operator can select one of the provided successive approximation process levels. Alternatively, when inputting the successive approximation process level to the input area 310 in FIG. 4, if the operator inputs a successive approximation process level exceeding the limit level through a keyboard or the like, for example, a warning message is sent to attract attention, so that the setting of the successive approximation process level exceeding the limit level is disabled. In the case of setting the setting conditions so that the operator can input the numerical values of the limit level or less while observing the table 600 of the limit level according to the examination purpose, a "limit level" display may be given on the screen of FIG. 4(A) together with the "confirm" display 301 and the "type change" display 303 so that the table 600 of the limit level is displayed when the display is clicked, or the table 600 of the limit level may be displayed together with FIG. 4(A) by default.

As described above, when selecting the level of the successive approximation process, the limit level is provided according to the examination purpose. Therefore, it is possible to prevent the edge blurring of an image by setting the limit level in advance and to perform scanning that avoids excessive low-dose scanning. By presenting the limit level, it is possible to appropriately set a scanning condition that matches the condition of the object, in particular, a tube current value. As a result, it is possible to relatively easily obtain an image with desirable image quality according to the state of the object.

Fourth Embodiment

Figure 23:
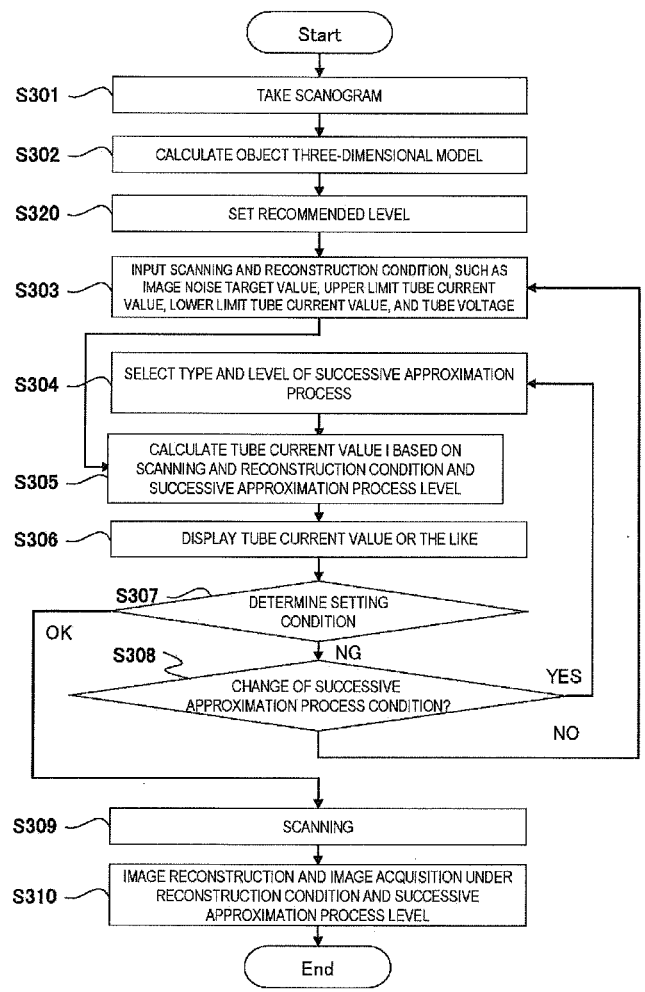
FIG. 23 is a diagram for explaining the flow of the process in a fourth embodiment.

FIG. 23 is a diagram showing an operation according to a fourth embodiment of the present invention. The same steps as in FIG. 3 are denoted by the same step numbers. Differences from the first to third embodiments are that a successive approximation process level recommended in step S320 (hereinafter, a recommended level) is presented to the operator and is automatically set as a successive approximation process level by default. In this case, instead of automatic setting, it is also possible to make the operator see the presented recommended level and manually set the recommended level. In the third embodiment, since the limit level is presented in advance for each of a part, tube voltage, and weight in the table 600 in FIG. 22, the operator had to select a level equal to or less than the limit level. In the present embodiment, since the recommended level displayed in a table 700 in FIG. 24 is automatically (or manually) set, it is possible to further reduce the operation burden of the operator. The table 700 may be prepared for each successive approximation process type.

The recommended level is registered in advance in the scanning protocol according to the examination purpose. For example, FIG. 24 is a diagram showing an example of the setting screen for setting the recommended level in advance for each of a part, tube voltage, and weight. For example, the recommended level in the case of scanning an object when a part is a lung field and the weight is less than 40 kg is set to 5. The limit level shown in FIG. 22 is 7, and 5 that is a value lower than 7 is set as the recommended level. As another example, the recommended level in the case of scanning an object when a part is abdomen, the tube voltage is 120 kV or more, and the weight is 80 kg or more is set to 2. The limit level shown in FIG. 22 is 3, and 2 that is a value lower than 3 is also set as the recommended level in this case. Similarly to other weights or parts, values lower than the limit levels are preferably set as the recommended levels.

The recommended level is not limited to a part, a tube voltage, and weight, and may be set using indicators, such as age, BMI, or minimum identification diameters required for diagnosis. For the weight, in the case of equipment in which a weight measurement mechanism is included in a bed or the like, the measured value may be read and used for case classification. If there is a function allowing the registration of the weight of the object at the time of CT examination, the weight may be input using the function so as to be used for case classification. Instead of the weight, cases may be classified according to the size of the three-dimensional model of the object calculated in S302. Instead of the weight, cases may be classified according to the size of the three-dimensional model of the object calculated in S302. Hereinafter, the setting of the recommended level in S320 will be described. Since other steps are the same as in FIG. 3, explanation thereof will be omitted.

In step S320, a recommended level is provided to the operator, so that the operator can select a level with reference to the recommended level. Specifically, recommended levels are provided in the input area 310 in FIG. 4, so that the recommended level is automatically set according to the condition set in advance in the table 700. Alternatively, in the case of setting the level, a "recommended level" display may be given on the screen of FIG. 4(A) together with the "confirm" display 301 and the "type change" display 303 so that the table 700 of the recommended level is displayed when the display is clicked, or the table 700 of the recommended level may be displayed together with FIG. 4(A) by default so that the operator manually inputs the numerical value of a level while observing the table 700 according to the examination purpose.

When it is determined that the successive approximation process level needs to be changed in step S308, an arbitrary successive approximation process level can be selected in step S304 as shown in the first embodiment. In this case, the table 600 of the limit level shown in FIG. 22 may be displayed as described in the third embodiment, or the table 700 of the recommended level shown in FIG. 24 may be displayed again.

From the above, since the operator can immediately use the successive approximation process level suitable for standard use, it is possible to perform an operation with reduced time and effort to select the successive approximation process level.

Fifth Embodiment

The second embodiment showed a method of avoid clipping by changing the successive approximation process level or changing the image noise target value or the CNR target value when clipping due to the upper limit tube current value occurred. However, the method of the second embodiment may cause excessive low-dose scanning. As also described in the third embodiment, excessive low dose scanning tends to cause edge blurring of an object, and may not be recommended. From such a background, a method of performing scanning while maintaining a certain degree of dose (tube current value) using the successive approximation process of low to middle level at the time of scanning is preferable in some cases rather than the excessive low-dose scanning using the successive approximation process of a high level. In this case, however, since the clipping due to the upper limit tube current value still occurs, a possibility that the image noise target value or the CNR target value cannot be achieved is high.

Therefore, in the present embodiment, a method is shown in which the image noise target value or the CNR target value is realized without changing the dose even if clipping due to the upper limit tube current value occurs.

Figure 25:
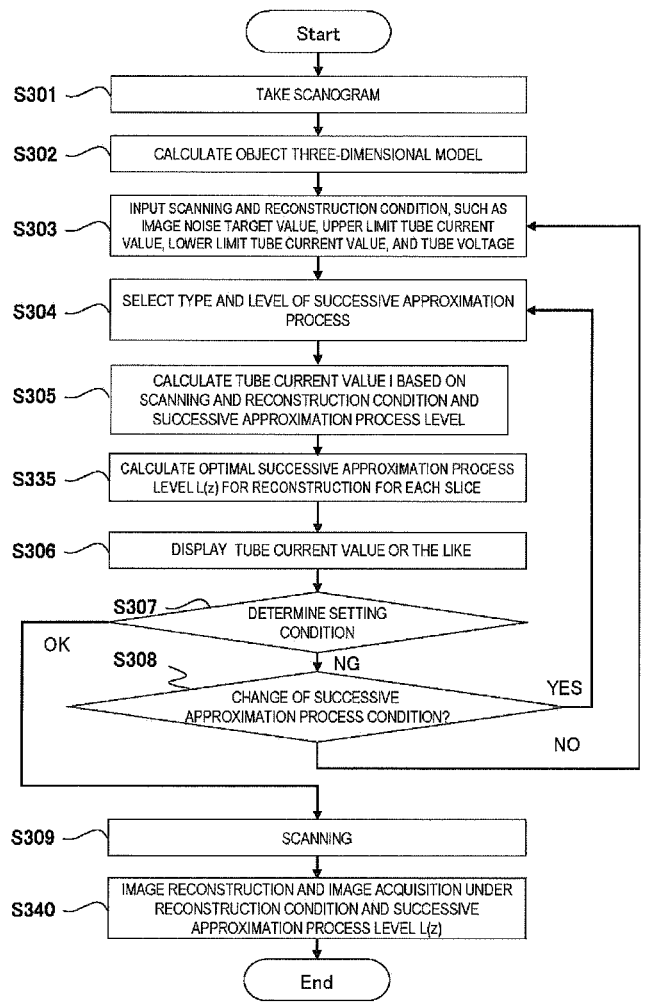
FIG. 25 is a diagram for explaining the flow of the process in a fifth embodiment.

FIG. 25 is a diagram showing an operation according to a fifth embodiment of the present invention. Since steps denoted by the same reference numerals as in FIG. 3 indicate approximately the same operations, detailed explanation thereof will be omitted.

In the same manner as in the first to fourth embodiments, in steps S303 and S304, the operator selects the scanning and reconstruction conditions and the successive approximation process level. As a setting screen, it is possible to use the same screen as the screen in FIG. 4(A). Basically, image reconstruction is performed based on the selected successive approximation process level. However, differences from the first to fourth embodiments are that the optimal successive approximation process level for reconstruction is further calculated for each slice in step S335 and is applied to the image reconstruction in step S340. In the third and fourth embodiments, the optimal successive approximation process level for reconstruction is set for each diagnostic purpose of the object and is applied to image reconstruction. However, for example, in the case of capturing the long scanning range from the lung field to abdomen by one-time scanning, the setting conditions should be narrowed down to either one of the lung field and the abdomen. For this reason, there has been a problem that the optimal condition is not applied for one of the parts.

In addition, in order to avoid this, it is necessary to set conditions separately for the lung field and the abdomen and perform scanning twice. Accordingly, there has been a problem that the operation to set the conditions is complicated or that it takes long time for scanning and accordingly the throughput is reduced. In the present embodiment, the optimal successive approximation process level for reconstruction for realizing the image noise target value or the CNR target value is calculated for each slice. Unlike the first to fourth embodiments, since image reconstruction is performed at the optimal successive approximation process level for each slice, it takes slightly longer time than in the image reconstruction in the first to fourth embodiments.

Figure 27:
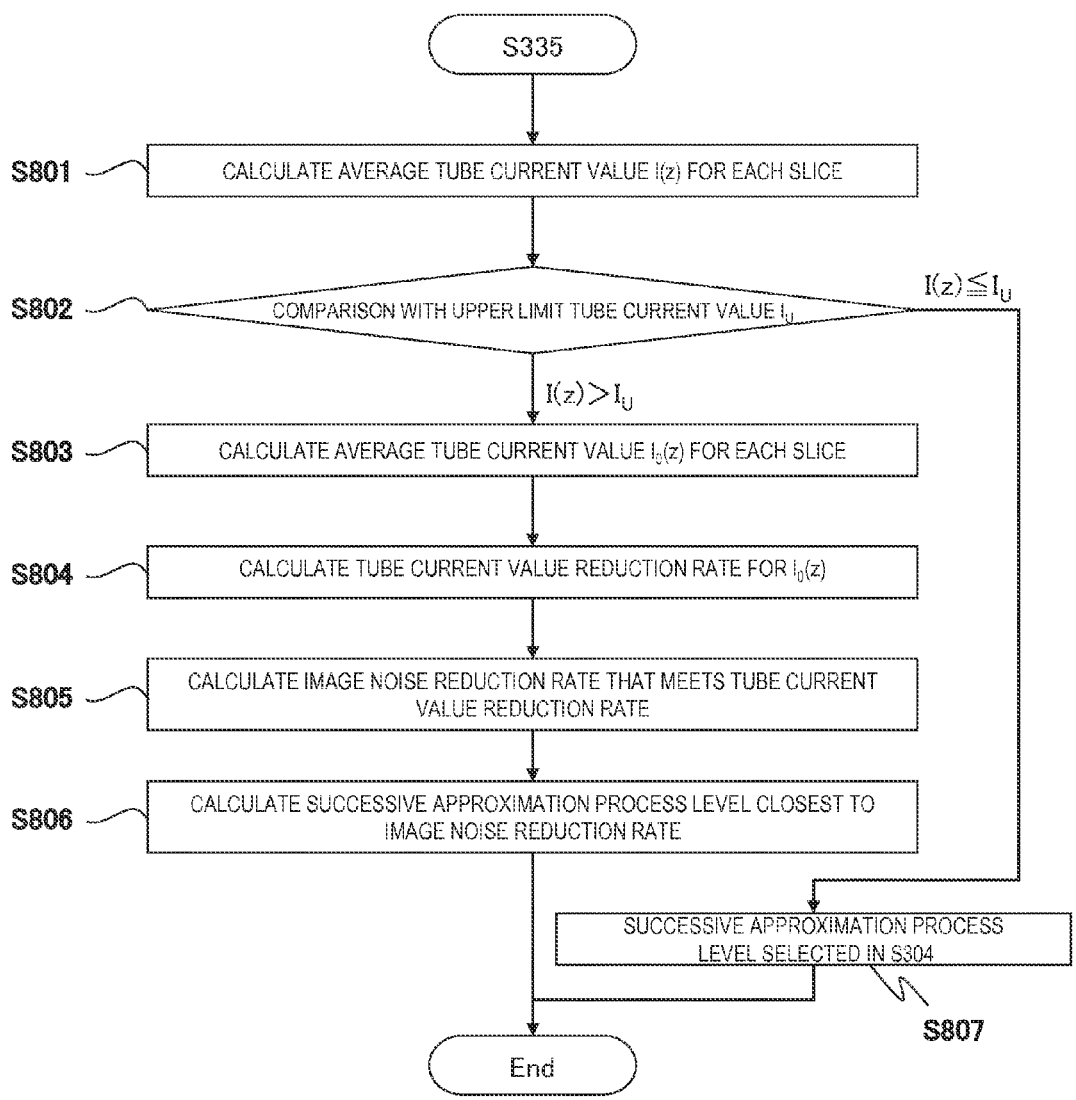
FIG. 27 is a diagram for explaining the flow of the process of S335 in FIG. 25 of the fifth embodiment.

Hereinafter, the SD mode will be described as an example. FIG. 26 is a tube current value graph(A) and a predicted image noise value graph (B) for explaining the process of step S335. As shown in FIG. 26(A), a case when performing scanning in a tube current value pattern 30 where clipping due to the upper limit tube current value has occurred will be described. In this case, image noise before the application of the successive approximation process shown in FIG. 26(B) becomes large in a slice in which the tube current value is insufficient as shown in a predicted image noise value pattern 31, that is, in a slice of a portion (251, 252) where clipping of the tube current value has occurred. Accordingly, the image noise before the application of the successive approximation process is not a fixed value. When the successive approximation process level selected in step S304 is applied to all slices in this state, image noise becomes larger than the image noise target value in the slice (251, 252) in which the tube current value is insufficient. Therefore, in step S335, in order to realize an image noise target value for the slice (251, 252) in which the tube current value is insufficient, an optimal successive approximation process level is calculated. FIG. 27 is a diagram showing the detailed operation in step S335. Hereinafter, the detailed operation in FIG. 27 will be described.

Step S801 will be described. An X-ray tube phase angle required to configure a slice position z is set to $\theta=\theta_1, \theta_2, \ldots, \theta_M$. An average tube current value I(z) required for each slice of a reconstructed image when the successive approximation process level selected in step S304 is taken into consideration is calculated according to the following expression. Here, a tube current value I(z, $\theta$) for each slice and phase angle is a theoretical operation value calculated in (Expression 6) or (Expression 13), and is assumed to be a tube current value at a level where the influence of clipping is not taken into consideration.

$$I(z) = \frac{1}{M} \sum_{\theta=\theta_1}^{\theta_M} I(z, \theta) \qquad \text{[Expression 14]}$$

In step S802, $I_U$ that is an upper limit tube current value set by the operator in step S303 is compared with the average tube current value I(z). For a slice (for example, slices of portions 251 and 252 in FIG. 26(A)) satisfying $I(z) > I_U$, that is, a condition in which the required tube current value exceeds the upper limit tube current value, the process proceeds to step S803. For a slice satisfying $I(z) \le I_U$, that is, a slice in which it is possible to perform scanning with the required tube current value, the process proceeds to step S807.

In step S803, for a slice in which it is not possible to perform scanning with the required tube current value, an average tube current value $I_0(z)$ for each slice when the successive approximation process is not taken into consideration is calculated according to the following expression.

$$I_0(z) = \frac{1}{M} \sum_{\theta=\theta_1}^{\theta_M} I_0(z, \theta) \qquad \text{[Expression 15]}$$

In step S804, in the portions 251 and 252 where clipping has occurred, when performing scanning by setting the tube current value I(z) to the upper limit tube current value $I_U$, a tube current value reduction rate R(z) for the tube current value $I_0(z)$ when the successive approximation process is not taken into consideration is calculated according to the following expression.

$$R(z) = \frac{I_0(z) - I_U}{I_0(z)} \qquad \text{[Expression 16]}$$

In step S805, in order to achieve the image noise target value, it is necessary to compensate for the tube current value reduction rate R(z) by applying the successive approximation process of a higher level in image reconstruction. An image noise reduction rate P(z) of the successive approximation process required to compensate for the tube current value reduction rate R(z) is calculated according to the following expression.

$$P(z) = 1 - \sqrt{1 - R(z)} \qquad \text{[Expression 17]}$$

In step S806, a successive approximation process level L(z) that can satisfy the image noise reduction rate P(z) is calculated. As the level, a level showing an image noise reduction rate closest to P(z) may be specified from N levels of a predetermined successive approximation process level $L_i$ (i=1, 2, ..., N) prepared in advance, or an optimal successive approximation process level showing the image noise reduction rate P(z) may be calculated without being limited to the predetermined levels. When P(z) indicates a value exceeding the maximum image noise reduction rate of the successive approximation process level, a successive approximation process level of the highest level is preferably assigned as a level showing the image noise reduction rate closest to P(z).

In step S807, for a slice in which it is possible to perform scanning with the required tube current value, it is not necessary to calculate the optimal successive approximation process level for each slice, and the successive approximation process level selected in step S304 is applied.

As described above, in step S335, an optimal successive approximation process level for reconstruction L(z) is calculated for each slice. The operator determines whether or not the setting conditions are proper in step S307 while checking whether or not the predicted image noise value pattern displayed in step S306 (for example, a predicted image noise value pattern 32 in FIG. 26(B)) satisfies the image noise target value.

In step S340, image reconstruction is performed according to the setting conditions regarding the image reconstruction set in step S303 and the optimal successive approximation process level L(z) for each slice set in step S335. By performing image reconstruction using L(z), it is possible to realize an image noise target value, such as the predicted image noise value pattern 32 after the application of the successive approximation process in FIG. 26(B).

As described above, in the present embodiment, even when performing scanning with a tube current value with which clipping due to the upper limit tube current value has occurred, it is possible to realize the image noise target value or the CNR target value by resetting the successive approximation process level optimally at the time of reconstruction of a portion where clipping has occurred.

Sixth Embodiment

Figure 28:
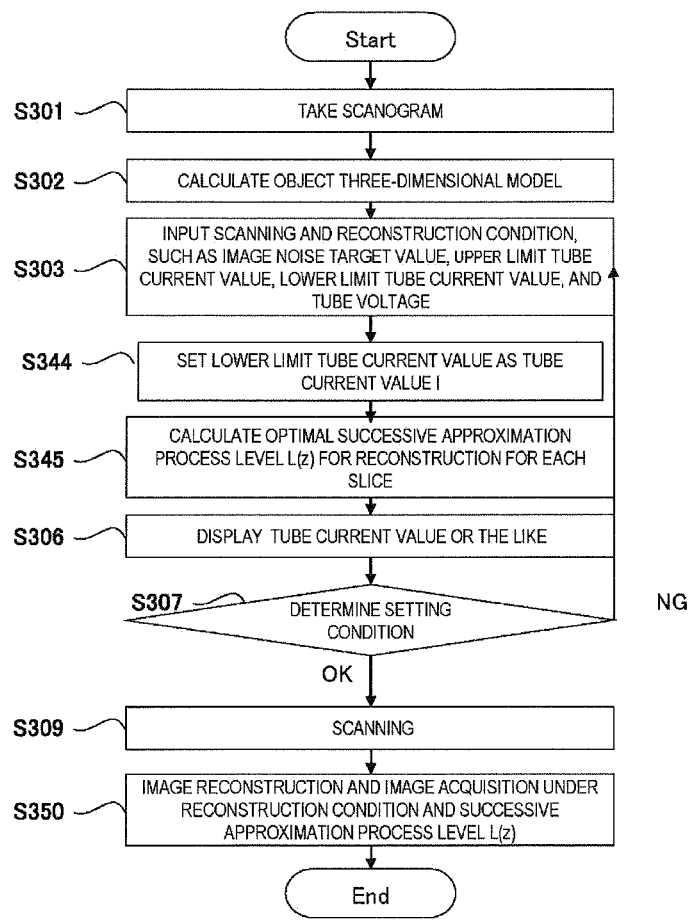
FIG. 28 is a diagram for explaining the flow of the process in a sixth embodiment.

FIG. 28 is a diagram showing an operation according to a sixth embodiment of the present invention. The same steps as in FIG. 3 are denoted by the same step numbers. Differences from the first to fifth embodiments are that the lower limit tube current value set as the tube current value I by the operator in step S344 is set without the operator setting the successive approximation process level and that the optimal successive approximation process level for reconstruction is calculated so as to realize the image noise target value or the CNR target value for each slice in step S345 and is applied for the image reconstruction in step S350. In the present embodiment, since the tube current value is set to the lower limit tube current value, it is possible to perform scanning with a low dose. Therefore, the present invention can be used in the medical examination to examine a healthy object.

In the same manner as in the first to fifth embodiments, in step S303, the operator inputs scanning and reconstruction conditions on the setting screen in FIG. 4(A). Since the successive approximation process level is not selected in the present embodiment, the column of the successive approximation process level may be removed from the input area 310.

Hereinafter, the SD mode will be described as an example. FIG. 29 is a tube current value graph (A) and a predicted image noise value graph (B) for explaining the process of steps S344 and S345. A case when performing scanning in a tube current value pattern 40 by the lower limit tube current value in FIG. 29(A) will be described.

In step S344, a lower limit tube current value $I_L$ set by the operator in step S303 is substituted into the tube current value I. When it is necessary to avoid excessive low-dose scanning, it is preferable to adjust the setting value of the lower limit tube current value.

$$I = I_L \quad \text{[Expression 18]}$$

In step S345, when performing scanning with the fixed tube current value of (Expression 18), image noise before the application of the successive approximation process becomes large in a slice in which the tube current value is insufficient as shown in a predicted image noise value pattern 42. Accordingly, the image noise before the application of the successive approximation process is not a fixed value. Therefore, in order to apply a different successive approximation process level for each slice according to the tube current value that is insufficient, the optimal successive approximation process level for reconstruction L(z) is calculated.

Figure 30:
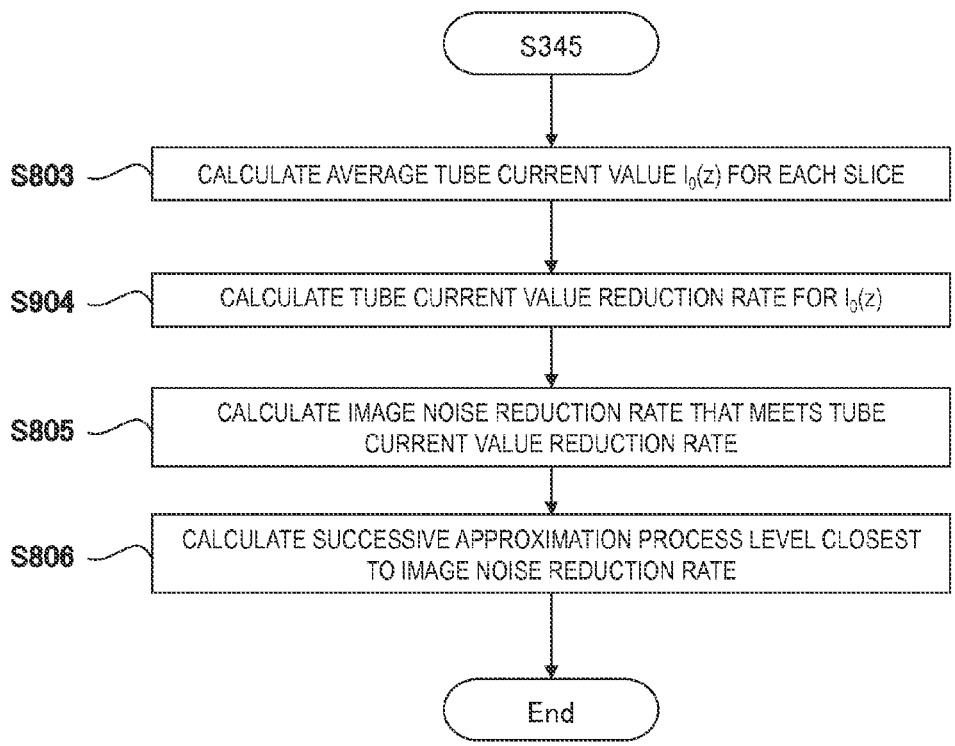
FIG. 30 is a diagram for explaining the flow of the process of S345 in FIG. 28 of the sixth embodiment.

FIG. 30 is a diagram showing the detailed operation in step S345. The same reference numerals as in FIG. 27 indicate approximately the same operations.

In step S904, when performing scanning with the lower limit tube current value $I_L$, a tube current value reduction rate R(z) for the tube current value $I_0(z)$ (tube current value pattern 41 in FIG. 29(A)) when the successive approximation process is not taken into consideration is calculated according to the following expression.

$$R(z) = \frac{I_0(z) - I_L}{I_0(z)} \quad \text{[Expression 19]}$$

Since other steps are the same as in FIG. 27, explanation thereof will be omitted.

As described above, in step S345, the optimal successive approximation process level for reconstruction L(z) is calculated for each slice. The operator determines whether or not the setting conditions are proper in step S307 while checking whether or not the predicted image noise value pattern displayed in step S306 (for example, a predicted image noise value pattern 43 in FIG. 29(B)) satisfies the image noise target value. For example, when the predicted image noise value pattern exceeds the image noise target value, it is preferable to set the lower limit tube current value to a high value or set a higher image noise target value in order to ensure a certain degree of dose. In this case, a recommended condition may be displayed as in the second embodiment.

In the same manner as in the fifth embodiment, in step S350, image reconstruction is performed according to the setting conditions regarding the image reconstruction set in step S303 and the optimal successive approximation process level L(z) for each slice set in step S345. By performing image reconstruction using L(z), it is possible to realize an image noise target value, such as the predicted image noise value pattern 43 after the application of the successive approximation process in FIG. 29(B).

From the above, it is possible to realize the image noise target value or the CNR target value after reducing the exposure as much as possible. Since the operator can set the lower limit tube current value while checking the predicted image noise value pattern, there is no concern for lowering the dose excessively. In addition, since the level of the successive approximation process is optimally controlled for each slice position, the operator can save the time and effort to select the successive approximation process level.

According to the first to sixth embodiments described above, even when the successive approximation process is applied, it is possible to realize an image having image noise or the CNR that the operator desires. In addition, by using the image noise reduction effect of the successive approximation process, it is possible to reduce the exposure of the object more than in the conventional X-ray automatic exposure mechanism.

In addition, when inputting the scanning and reconstruction conditions on the setting screen in FIG. 4(A), the level can be set (or the level is set automatically) by referring to the recommended condition or the limit level in FIGS. 18, 22, and 24 or the like. Since this method is convenient for use, this is excellent in operability.

While the embodiments of the present invention have been described, the present invention is not limited thereto.

REFERENCE SIGNS LIST

1: X-ray CT apparatus
71 to 74: portion where clipping of tube current value occurs
90: curve showing image noise for tube current value
92: tube current value reduction
94: image noise reduction
100: scan gantry unit
101: X-ray tube
102: rotary disk
103: collimator
104: opening
105: bed
106: X-ray detector
107: data collection device
108: gantry controller
109: bed controller
110: X-ray controller
120: console
121: input device
122: image reconstruction device
123: storage device
124: system controller
125: display device
181, 182: portion where clipping of tube current value occurs
201: scanogram taking control unit
202: three-dimensional model generation unit
203: condition setting unit
204: tube current value calculation unit
205: tube current value display control unit
206: scanning control unit
207: image reconstruction control unit
208: image display control unit
251, 252: portion where clipping of tube current value occurs
300: display screen
301: confirm display
303: type change display
310: input area
320: output area
400: selection screen
500: numerical comparison table
600: table of limit level
700: table of recommended level

The invention claimed is:

1. An X-ray CT apparatus, comprising:
an X-ray source that includes an X-ray tube and emits X-rays to an object;

an X-ray detector that detects transmitted X-rays that have been emitted from the X-ray source and transmitted through the object;

a rotation mechanism in which the X-ray source and the X-ray detector are mounted and which rotates around the object;

a system controller to control the X-ray CT apparatus and including:
- a tube current value calculation unit to calculate a tube current value of the X-ray tube based on a successive approximation process condition selected from a plurality of successive approximation process conditions and a received input of a scanning condition and/or a reconstruction condition;
- a scanning control unit to perform scanning in accordance with the calculated tube current value of the X-ray tube; and
- an image reconstruction control unit to control reconstruction of a tomographic image of the object; and an image reconstruction device controlled by the image reconstruction control unit of the system controller to reconstruct the tomographic image of the object, in accordance with the selected successive approximation process condition and the received input of the reconstruction condition, from an amount of transmitted X-rays detected by the X-ray detector after being emitted from the X-ray source to the object in accordance with the calculated tube current value of the X-ray tube and being transmitted through the object.

2. The X-ray CT apparatus according to claim 1,
wherein the system controller further includes a three-dimensional model generation unit to generate a cross-section model or a three-dimensional model of the object, and wherein the tube current value calculation unit uses the cross-section model or the three-dimensional model when calculating the tube current value.

3. The X-ray CT apparatus according to claim 1,
wherein the system controller further includes a tube current value display control unit,
wherein the tube current value calculation unit of the system controller calculates the tube current value of the X-ray tube based on the successive approximation process condition selected from the plurality of successive approximation process conditions, and the tube current value display control unit of the system controller displays a calculation result on a display unit, and wherein the tube current value calculation unit newly calculates the tube current value of the X-ray tube based on a newly selected successive approximation process condition when the successive approximation process condition different from the selected one is newly selected and the tube current value display control unit displays the calculation result on the display unit, and wherein the scanning control unit of the system controller performs scanning with the tube current value of the X-ray tube calculated based on the determined successive approximation process condition when the successive approximation process condition is determined, and wherein the image reconstruction device controlled by the image reconstruction control unit of the system controller reconstructs the tomographic image of the object, based on the determined successive approximation process condition and the reconstruction condition, from the amount of transmitted X-rays detected by the X-ray detector by the scanning.

4. The X-ray CT apparatus according to claim 1,
wherein the system controller further includes:
- a condition setting unit to receive and set an upper limit value and/or a lower limit value of the tube current value of the X-ray tube, as a part of the scanning condition; and
- a tube current value display control unit to create a tube current value graph in which one axis indicates the tube current value of the X-ray tube and the other axis indicates a body axis of the object, to display the upper limit value of the tube current value of the X-ray tube and/or the lower limit value of the tube current value of the X-ray tube in the tube current value graph on a display unit, and to display the calculated tube current value of the X-ray tube in the tube current value graph on the display unit.

5. The X-ray CT apparatus according to claim 4,
wherein, when a clipping state in which the calculated tube current value of the X-ray tube reaches the upper limit value and/or the lower limit value occurs in the tube current value graph created by the system controller, the clipping state is displayed in the tube current value graph on the display unit.

6. The X-ray CT apparatus according to claim 2,
wherein the system controller further includes a condition setting unit to receive and set (i) an image noise target value that is a target value of an image noise value or (ii) a CNR target value that is a target value of a contrast noise ratio, as a part of the scanning condition, and wherein the system controller creates an image noise graph in which one axis indicates image noise of the tomographic image and the other axis indicates a body axis of the object, displays the image noise target value in the image noise graph on a display unit, and displays on the display unit a predicted value of the image noise value obtained by calculation based on the three-dimensional model, the selected successive approximation process condition, the scanning condition, and the reconstruction condition, or the system controller creates a CNR graph in which one axis indicates a CNR of the tomographic image and the other axis indicates a body axis of the object, displays the CNR target value in the CNR graph on the display unit, and displays on the display unit a predicted value of the CNR obtained by calculation based on the three-dimensional model the selected successive approximation process condition, the scanning condition, and the reconstruction condition.

7. The X-ray CT apparatus according to claim 1,
wherein, based on a clipping state of the tube current value of the X-ray tube calculated by the tube current value calculation unit of the system controller, when the successive approximation process condition is newly selected in order to reduce the clipping state, the tube current value calculation unit of the system controller newly calculates the tube current value of the X-ray tube based on the newly selected successive approximation process condition, and the scanning control unit of the system controller performs scanning with the newly calculated tube current value of the X-ray tube, and the image reconstruction device controlled by the image reconstruction control unit of the system controller reconstructs the tomographic image of the object, based on the newly selected successive approximation process condition and the reconstruction condition, from the amount of transmitted X-rays detected by the X-ray detector by the scanning.

8. The X-ray CT apparatus according to claim 1,
wherein the tube current value of the X-ray tube is calculated by the tube current value calculation unit based on the selected successive approximation process condition and a tube voltage supplied to the X-ray tube.

9. The X-ray CT apparatus according to claim 1,
wherein the tube current value of the X-ray tube is calculated by the tube current value calculation unit based on the selected successive approximation process condition and a field-of-view size.

10. The X-ray CT apparatus according to claim 1,
wherein the tube current value of the X-ray tube is calculated by the tube current value calculation unit based on the selected successive approximation process condition and image noise.

11. The X-ray CT apparatus according to claim 1,
wherein, for the tube current value of the X-ray tube calculated by the tube current value calculation unit based on the selected successive approximation process condition, the system controller displays a recommended condition of the successive approximation process condition on a display unit, and
when a successive approximation process condition is newly selected, the tube current value calculation unit of the system controller calculates the tube current value of the X-ray tube based on the newly selected successive approximation process condition.

12. The X-ray CT apparatus according to claim 1,
wherein the system controller further includes a tube current value display control unit to display, for the calculated tube current value of the X-ray tube, a recommended condition of an image noise target value on a display unit, and
when a new image noise target value is input, the tube current value calculation unit of the system controller calculates the tube current value of the X-ray tube based on the newly input image noise target value.

13. The X-ray CT apparatus according to claim 1,
wherein the system controller further includes a tube current value display control unit to display, for the calculated tube current value of the X-ray tube, a recommended condition of a CNR target value on a display unit, and
when a new CNR target value is input, the tube current value calculation unit of the system controller calculates the tube current value of the X-ray tube based on the newly input CNR target value.

14. The X-ray CT apparatus according to claim 1, wherein the system controller further includes:
a condition setting unit to receive input of, and specify, a preferred level range for the object or a diagnostic purpose, as a part of the successive approximation process condition, from a plurality of successive approximation process levels; and
a tube current value display control unit to display a level in the preferred level range or to display a limit level indicating a maximum value of the preferable level range, on a display unit.

15. The X-ray CT apparatus according to claim 1, wherein the system controller further includes:
a condition setting unit to receive input of, and specify, a preferred recommended level for the object or a diagnostic purpose, as a part of the successive approximation process condition, from a plurality of successive approximation process levels; and
a tube current value display control unit to display the recommended level on a display unit.

16. The X-ray CT apparatus according to claim 1, wherein the system controller further includes a condition setting unit to receive and set an upper limit value of the tube current of the X-ray tube, as a part of the successive approximation process condition and the scanning condition,
wherein when occurrence of a clipping state is predicted in which the calculated tube current value of the X-ray tube reaches the upper limit value, the system controller divides at least a portion of the object, in which the occurrence of the clipping state is predicted, into a plurality of positions along a body axis direction, specifies a successive approximation process condition for reconstruction corresponding to each of the positions, and the scanning control unit of the system controller performs scanning with the calculated tube current value of the X-ray tube, and
wherein the image reconstruction device controlled by the image reconstruction control unit of the system controller reconstructs the tomographic image of the object, in accordance with the successive approximation process condition for reconstruction corresponding to each of the positions and the received input of the reconstruction condition, from the amount of transmitted X-rays detected by the X-ray detector by the scanning.

17. An X-ray CT apparatus, comprising:
an X-ray source that includes an X-ray tube and emits X-rays to an object;
an X-ray detector that detects transmitted X-rays that have been emitted from the X-ray source and transmitted through the object;
a rotation mechanism in which the X-ray source and the X-ray detector are mounted and which rotates around the object;
a system controller that calculates a successive approximation process condition for reconstruction with respect to each of positions divided along a body axis direction of the object, from an image noise reduction rate of a successive approximation process, based on a received input of a scanning condition and/or a reconstruction condition and a predetermined tube current value of the X-ray tube, the system controller including:
a scanning control unit to perform scanning in accordance with the predetermined tube current value of the X-ray tube; and
an image reconstruction control unit to reconstruct a tomographic image of the object; and
an image reconstruction device controlled by the image reconstruction control unit of the system controller to reconstruct the tomographic image of the object, in accordance with the reconstruction condition and the successive approximation process condition for reconstruction corresponding to each of the positions for each scanning position, from an amount of transmitted X-rays detected by the X-ray detector after being emitted from the X-ray source to the object in accordance with the tube current value and being transmitted through the object.

18. A tomography method of an X-ray CT apparatus including an X-ray source that includes an X-ray tube and emits X-rays to an object, an X-ray detector that detects transmitted X-rays that have been emitted from the X-ray source and transmitted through the object, a rotation mechanism in which the X-ray source and the X-ray detector are mounted and which rotates around the object, a system controller including a tube current value calculation unit to calculate a tube current value of the X-ray tube and a scanning control unit to perform scanning, and an image reconstruction device controlled by an image reconstruction control unit of the system controller to reconstruct a tomographic image of the object from an amount of transmitted X-rays detected by the X-ray detector, the method comprising:

- a first step in which a successive approximation process condition selected from a plurality of successive approximation process conditions is input via a display to a condition setting unit of the system controller;
- a second step in which a scanning condition and a reconstruction condition are further input via a display to a condition setting unit of the system controller;
- a third step in which the tube current value calculation unit of the system controller calculates a tube current value of the X-ray tube based on the selected successive approximation process condition and the input scanning condition and/or the reconstruction condition;
- a fourth step in which the scanning control unit of the system controller performs scanning in accordance with the calculated tube current value of the X-ray tube; and
- a fifth step in which the image reconstruction device is controlled by the image reconstruction control unit of the system controller to reconstruct a tomographic image of the object, in accordance with the selected successive approximation process condition and the reconstruction condition, from an amount of transmitted X-rays detected by the X-ray detector after being emitted from the X-ray source to the object in accordance with the tube current value and being transmitted through the object.

* * * * *